(12) United States Patent
Mukkamala et al.

(10) Patent No.: US 10,398,324 B2
(45) Date of Patent: Sep. 3, 2019

(54) METHOD AND APPARATUS FOR CUFF-LESS BLOOD PRESSURE MEASUREMENT IN A MOBILE DEVICE

(71) Applicant: Board of Trustees of Michigan State University, East Lansing, MI (US)

(72) Inventors: Ramakrishna Mukkamala, Okemos, MI (US); Anand Chandrasekhar, East Lansing, MI (US); Jin-Oh Hahn, Rockville, MD (US)

(73) Assignees: Board of Trustees of Michigan State University, East Lansing, MI (US); University of Maryland, College Park, College Park, MD (US)

( * ) Notice: Subject to any disclaimer, the term of this patent is extended or adjusted under 35 U.S.C. 154(b) by 0 days.

(21) Appl. No.: 16/118,530

(22) Filed: Aug. 31, 2018

(65) Prior Publication Data

US 2019/0008399 A1  Jan. 10, 2019

Related U.S. Application Data

(63) Continuation-in-part of application No. PCT/US2017/020739, filed on Mar. 3, 2017.
(Continued)

(51) Int. Cl.
*A61B 5/00* (2006.01)
*A61B 5/021* (2006.01)
(Continued)

(52) U.S. Cl.
CPC ........ *A61B 5/02141* (2013.01); *A61B 5/0261* (2013.01); *A61B 5/0295* (2013.01);
(Continued)

(58) Field of Classification Search
CPC ... A61B 5/0077; A61B 5/0261; A61B 5/0295; A61B 5/706; A61B 5/743; A61B 5/6898;
(Continued)

(56) References Cited

U.S. PATENT DOCUMENTS

| | | | |
|---|---|---|---|
| 5,423,322 | A | 6/1995 | Clark et al. |
| 5,649,536 | A | 7/1997 | Ogura et al. |

(Continued)

FOREIGN PATENT DOCUMENTS

| | | |
|---|---|---|
| EP | 0694283 A2 | 1/1996 |
| KR | 10-0660349 B1 | 12/2006 |

(Continued)

OTHER PUBLICATIONS

Xia-Fei Teng, et al "Theoretical Study on the Effect of Sensor Contact Force on Pulse Transit Time", IEEE Transactions on Biomedical Engineering, vol. 54, No. 8, (Aug. 2007).
(Continued)

*Primary Examiner* — Boniface N Nganga
(74) *Attorney, Agent, or Firm* — Harness, Dickey & Pierce, PLC

(57) ABSTRACT

A system and method is presented for cuff-less blood pressure measurement in a mobile device. A key aspect of this disclosure is the discovery of a new location for blood pressure measurement at the fingertip of a subject and that reflectance-mode photoplethysmography can be used to help make this measurement. Through experiments in human subjects, it was discovered that it is indeed possible to measure systemic blood pressure by having a subject press the fingertip against a reflectance-mode photo-plethysmography-force sensor unit under visual guidance and then compute blood pressure from the resulting variable-amplitude blood volume oscillations and applied pressure via an oscillometric algorithm.

13 Claims, 18 Drawing Sheets

Related U.S. Application Data

(60) Provisional application No. 62/554,795, filed on Sep. 6, 2017, provisional application No. 62/555,028, filed on Sep. 6, 2017, provisional application No. 62/436,477, filed on Dec. 20, 2016, provisional application No. 62/303,074, filed on Mar. 3, 2016.

(51) Int. Cl.
*A61B 5/026* (2006.01)
*A61B 5/0205* (2006.01)
*A61B 5/0295* (2006.01)
*A61B 5/022* (2006.01)
*A61B 5/024* (2006.01)

(52) U.S. Cl.
CPC ...... *A61B 5/02225* (2013.01); *A61B 5/02416* (2013.01); *A61B 5/6898* (2013.01); *A61B 5/706* (2013.01); *A61B 5/743* (2013.01); *A61B 5/0077* (2013.01); *A61B 5/02055* (2013.01); *A61B 2560/0462* (2013.01); *A61B 2562/0238* (2013.01); *A61B 2562/0247* (2013.01)

(58) Field of Classification Search
CPC ............ A61B 5/02055; A61B 5/02141; A61B 2560/0462; A61B 2562/0247; A61B 2562/0238
See application file for complete search history.

(56) References Cited

U.S. PATENT DOCUMENTS

| | | | |
|---|---|---|---|
| 5,755,229 A | 5/1998 | Amano et al. | |
| 5,828,773 A | 10/1998 | Setlak et al. | |
| 6,231,517 B1 | 5/2001 | Forstner | |
| 7,179,228 B2 | 2/2007 | Banet | |
| 7,691,067 B2 | 4/2010 | Westbrook et al. | |
| 8,706,204 B2 | 4/2014 | Seo et al. | |
| 8,761,853 B2 | 6/2014 | Thaveeprungsriporn et al. | |
| 2003/0036685 A1 | 2/2003 | Goodman | |
| 2007/0055163 A1 | 3/2007 | Asada et al. | |
| 2007/0106163 A1 | 5/2007 | Friedman et al. | |
| 2007/0167844 A1 | 7/2007 | Asada et al. | |
| 2008/0077026 A1* | 3/2008 | Banet ................ A61B 5/02055 600/509 |
| 2008/0249382 A1 | 10/2008 | Oh et al. | |
| 2010/0286539 A1 | 11/2010 | Ito et al. | |
| 2010/0298656 A1 | 11/2010 | McCombie et al. | |
| 2011/0105918 A1 | 5/2011 | Fortin et al. | |
| 2011/0215341 A1 | 9/2011 | Bond et al. | |
| 2011/0300847 A1* | 12/2011 | Quy ........................ H04W 4/00 455/419 |
| 2012/0071734 A1 | 3/2012 | Shimuta et al. | |
| 2012/0203119 A1 | 8/2012 | Yamashita et al. | |
| 2013/0072145 A1 | 3/2013 | Dantu | |
| 2014/0066793 A1 | 3/2014 | Mukkamala et al. | |
| 2014/0221847 A1 | 8/2014 | Dubielczyk et al. | |
| 2014/0364711 A1 | 12/2014 | Ismail et al. | |
| 2015/0073239 A1 | 3/2015 | Pei et al. | |
| 2015/0261996 A1* | 9/2015 | Kim .................... G06K 9/00255 348/14.03 |
| 2015/0374249 A1* | 12/2015 | Elliott ................ A61B 5/14532 600/301 |
| 2016/0198955 A1* | 7/2016 | Fortin .................... A61B 5/021 600/323 |

FOREIGN PATENT DOCUMENTS

WO  WO-2012099535 A1 *  7/2012  ......... G01N 21/3151
WO  WO-2014/168718 A1  10/2014

OTHER PUBLICATIONS

X.F. Teng et al "The effect of applied sensor contact force on pulse transit time", Physiol. Meas. 27, pp. 675-684 (2006).

* cited by examiner

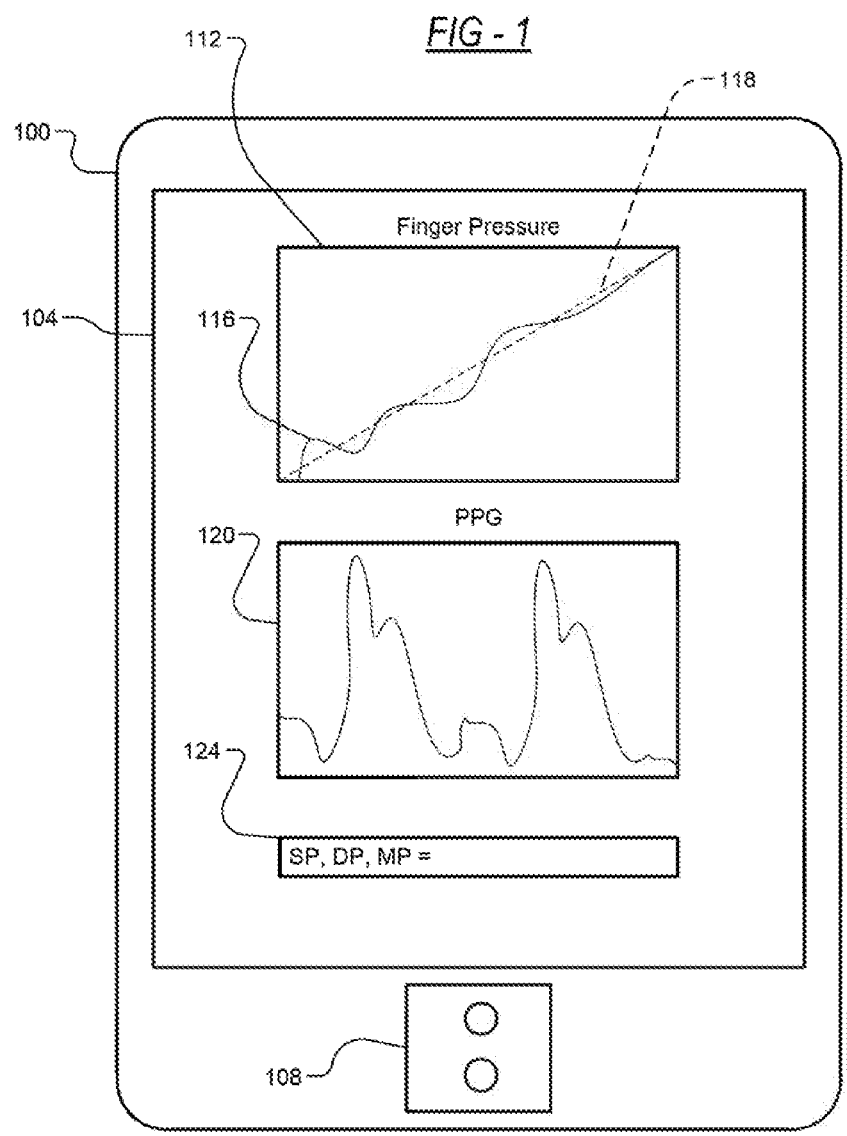

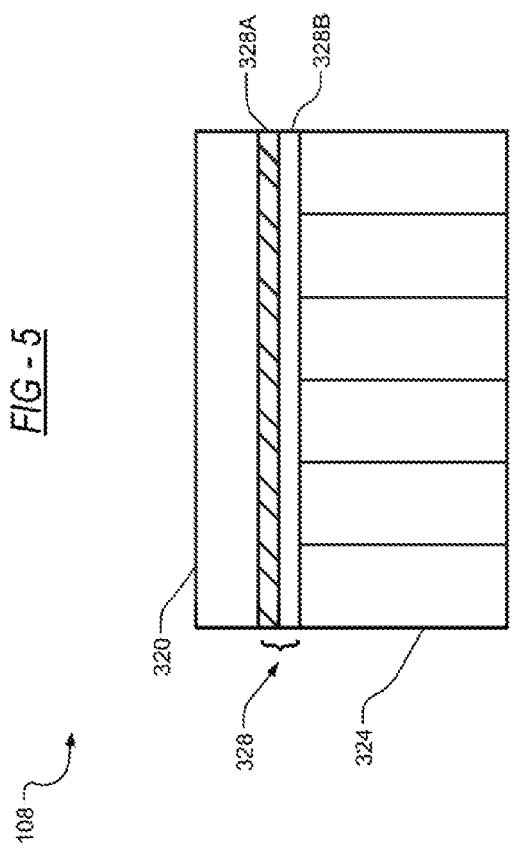

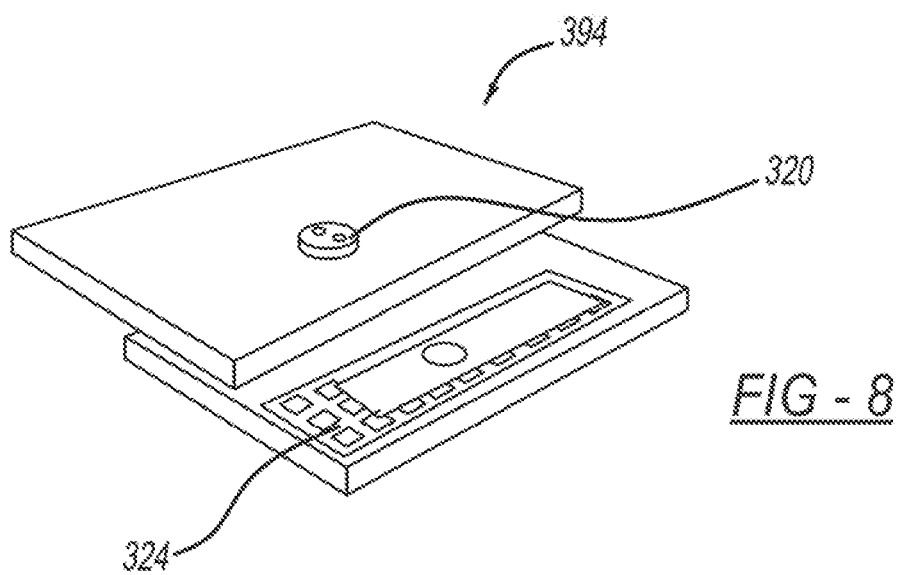

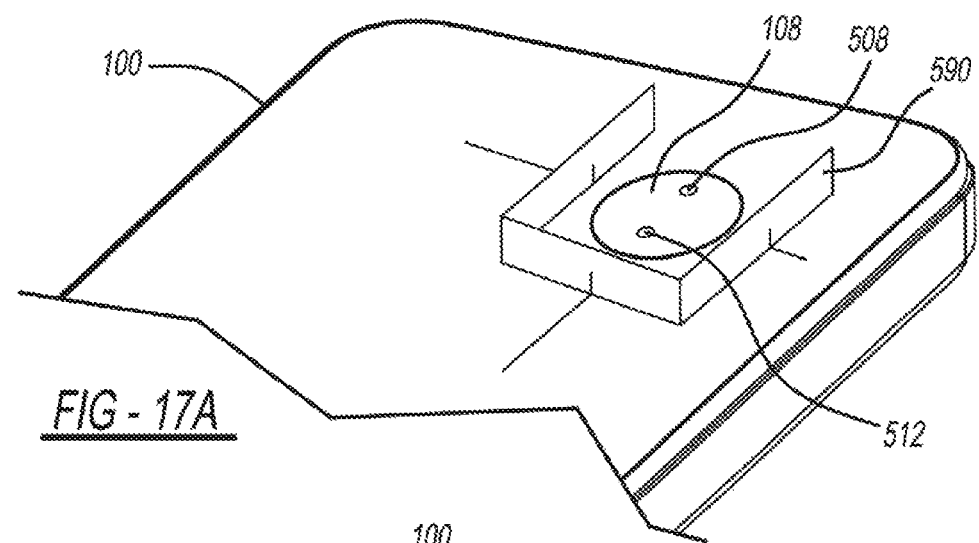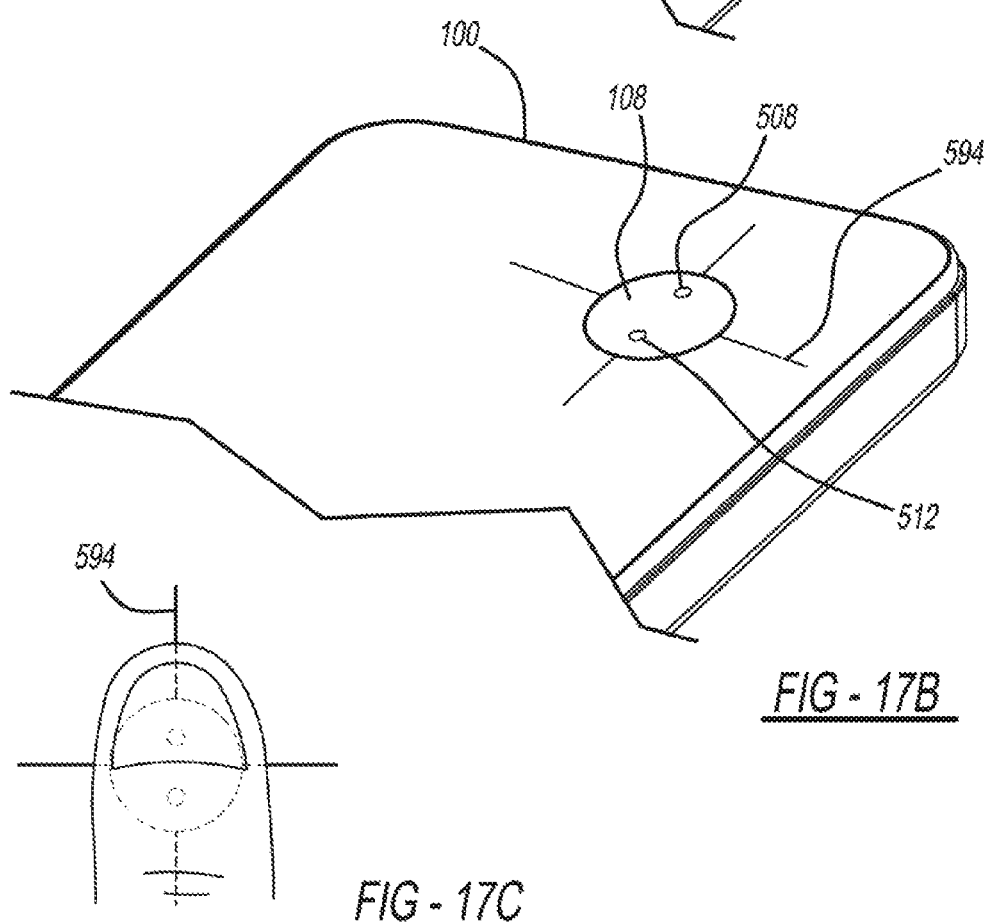

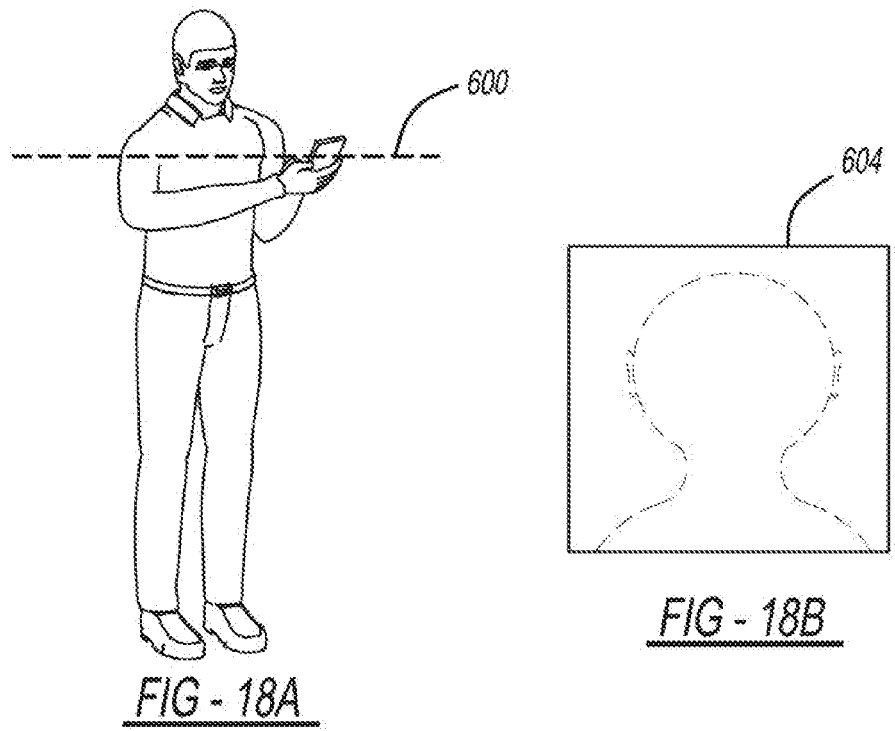
FIG - 18A
FIG - 18B
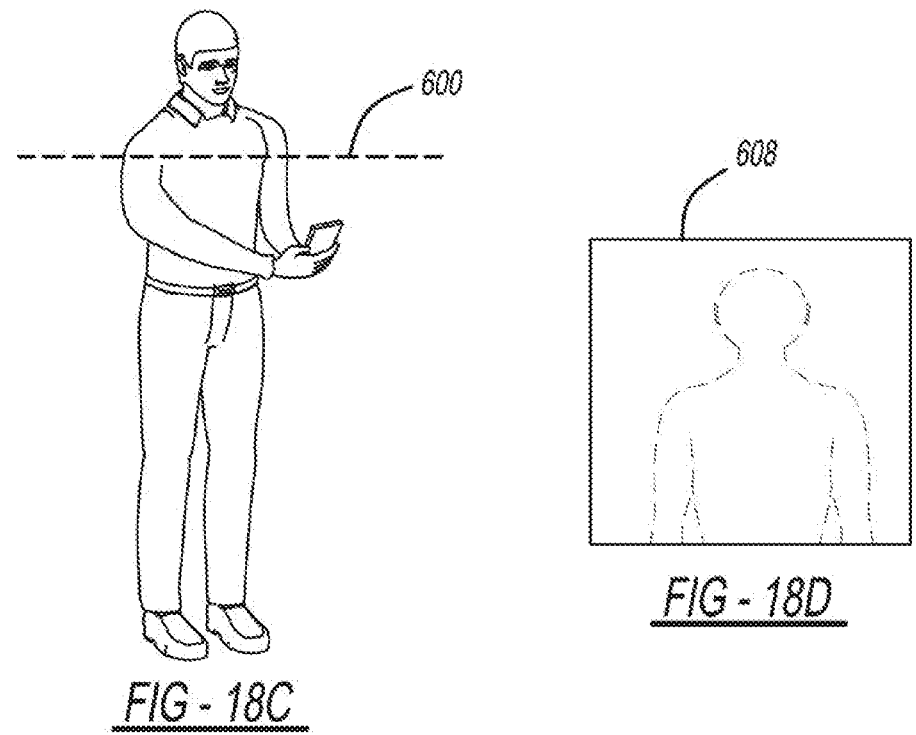
FIG - 18C
FIG - 18D

METHOD AND APPARATUS FOR CUFF-LESS BLOOD PRESSURE MEASUREMENT IN A MOBILE DEVICE

CROSS-REFERENCE TO RELATED APPLICATIONS

The present application is a continuation-in-part of and claims the benefit of priority to International Application No. PCT/US2017/020739, filed Mar. 3, 2017, which in turn claims the benefit of U.S. Provisional Application No. 62/303,074, filed Mar. 3, 2016 and U.S. Provisional Application No. 62/436,477, filed Dec. 20, 2016. The present application also claims the benefit of U.S. Provisional Application No. 62/555,028, filed Sep. 6, 2017 and U.S. Provisional Application No. 62/554,795 filed Sep. 6, 2017. The entire disclosures of the applications referenced above are incorporated by reference.

GOVERNMENT CLAUSE

This invention was made with government support under EB018818 awarded by the National Institutes of Health. The government has certain rights in the invention.

FIELD

The present disclosure relates to a method of cuff-less blood pressure measurements in a mobile device.

BACKGROUND

Hypertension afflicts about one-fourth of the world's adult population. It is a major risk factor for stroke and heart disease and is therefore a "silent killer". Hypertension can be treated with lifestyle changes and medication. Medical therapy is associated with a 35-40% reduction in the risk of stroke and a 15-25% reduction in the risk of heart disease. Hence, hypertension management is an archetypical example of preventive, proactive healthcare. However, the detection of high blood pressure (BP) is often missed. An estimated 20% of people with hypertension in the US do not know they have it. Further, BP in known hypertensive patients is often uncontrolled. An estimated 53% of hypertensive patients in the US do not have their BP under control. Hypertension detection and control rates are much worse elsewhere, especially in low resource settings wherein personnel trained in BP measurement and the means for people to have their BP measured are lacking. Hypertension management is complicated by the well-known masked and white coat effects in the clinic and large BP variability amongst few measurements. In fact, ambulatory BP monitoring is now considered the gold standard for the diagnosis of high BP. Ubiquitous BP monitoring technology could improve hypertension detection by providing serial, out-of-clinic measurements in the mass population and could enhance hypertension control by providing continual feedback to the individual patient.

Several methods are available for measuring BP. However, none of these methods offers ubiquitous BP monitoring capabilities.

Catheterization is the gold standard method. This method measures a BP waveform by placing a strain gauge in fluid contact with blood. However, this method is invasive.

Auscultation is the standard clinical method. This method measures systolic BP (SP) and diastolic BP (DP) by occluding an artery with a cuff and detecting the Korotkoff sounds using a stethoscope and manometer during cuff deflation. The first sound indicates the initiation of turbulent flow and SP, while the fifth sound is silent and indicates the renewal of laminar flow and DP. The method is non-invasive but requires a skilled operator. Further, due to safety and ecological concerns, mercury manometers are being replaced with high maintenance aneroid manometers.

Oscillometry is the most popular non-invasive and automatic method. This method measures mean BP (MP), SP, and DP using an inflatable cuff with a sensor to record the pressure inside it. The recorded cuff pressure not only rises and falls with cuff inflation and deflation but also shows tiny oscillations indicating the pulsatile blood volume in the artery. The amplitude of these oscillations varies with the cuff pressure, as the arterial blood volume-transmural pressure relationship is nonlinear. Transmural pressure of an artery is defined as the internal pressure (i.e., BP) minus the external pressure (cuff pressure in this case). The BP values are estimated from the oscillogram (i.e., the oscillation amplitudes versus the cuff pressure) using an algorithm (e.g., fixed-ratios). However, automatic cuffs do not afford ubiquitous BP monitoring capabilities. That is, people in low resource settings may not have any access to such devices; others must go out of their way (e.g., to a pharmacy) to use these devices; and even people who own a device cannot carry and use them outside their homes.

Volume clamping is a non-invasive and automatic method used in research. This method measures a finger BP waveform by using a cuff with a photoplethysmography (PPG) sensor built-in to measure the blood volume. The blood volume at zero transmural pressure is estimated by slowly varying the cuff pressure. The cuff pressure is then continually varied to maintain this blood volume throughout the cardiac cycle via a fast servo-control system. The applied cuff pressure may thus equal BP. However, in addition to requiring a cuff, the method is prohibitively expensive.

Tonometry is another research method. This method measures a BP waveform by pressing a manometer-tipped probe on an artery. The probe must flatten or applanate the artery so that its wall tension is perpendicular to the probe. However, manual and automatic applanation have proven difficult. As a result, while the method should not require any calibration, the measured waveform has been routinely calibrated with a cuff in practice. Furthermore, the method is likewise costly.

As a result, cuff-less BP monitoring technology is being widely pursued. Much of these efforts are based on the principle of pulse transit time (PTT). PTT is the time delay for the pressure wave to travel between two arterial sites. An increase in BP causes the arteries to stiffen which, in turn, causes PTT to decline. So, PTT is often inversely correlated with BP in individual subjects. Further, PTT may be simply determined from the relative timing between proximal and distal arterial waveforms. Hence, PTT carries the advantage of possibly offering passive BP monitoring without using a cuff. However, this approach also has major disadvantages. Firstly, PTT not only changes with BP but also smooth muscle contraction (especially when measured in small arteries) and aging and disease (especially when measured in large arteries). Smooth muscle contraction occurs acutely and thus severely limits the accuracy of the approach, whereas aging and disease are longer processes that prevent PTT from being able to track chronic changes in BP such as the common development of isolated systolic hypertension due to large artery stiffening with aging. Secondly, the required calibration of PTT in units of msec to BP in units of mmHg must either be population-based and thus error-prone or involve periodic use of a BP cuff and thus not truly cuff-less.

In sum, hypertension is a major cardiovascular risk factor that is treatable, yet high BP detection and control rates are unacceptably low. Ubiquitous BP monitoring technology could improve hypertension management, but oscillometric and other available non-invasive BP measurement devices employ an inflatable cuff and therefore do not afford such monitoring capabilities. While the PTT approach could potentially permit cuff-less and passive BP monitoring, its accuracy will be limited due to confounding physiology and the need for calibration. Hence, there is a need in the art for a ubiquitous method for reliable, cuff-less measurement of BP.

This section provides background information related to the present disclosure, which is not necessarily prior art.

SUMMARY

A handheld mobile device that measures blood pressure is presented. The mobile device includes: a processor enclosed within a housing; a display unit integrated into an exterior surface of the housing; and a sensing unit integrated into an exterior surface of the housing. The sensing unit is configured to measure blood pressure at a fingertip of a user. The sensing unit includes a reflectance-mode photo-plethysmography (PPG) sensor configured to measure blood volume oscillations and a pressure sensor configured to measure pressure applied by the fingertip. A non-transitory computer-readable medium enclosed in the housing stores instructions that, when executed by the processor, cause the processor to: measure pressure applied to the sensing unit by a fingertip of a user, measure blood volume oscillations in the fingertip while varying pressure is being applied to the sensing unit by the fingertip, generate an oscillogram from the measured pressure and the measured blood volume oscillations, where the oscillogram plots amplitude of blood volume oscillations as a function of the measured pressure; calculate a blood pressure value from the oscillogram, and present the blood pressure value on the display unit.

The mobile device may include a visual guide disposed on the exterior surface and arrange in relation to the sensing unit. In one embodiment, the visual guide is further defined as indicia for placement of the fingertip in relation to the sensing unit.

The sensing unit may take on different forms. For example, the PPG sensor may be implemented by a light emitting diode cooperatively operating with a photodetector. Alternatively, the PPG sensor may be implemented as a camera. In some examples, the pressure sensor is placed on top of the PPG sensor as it relates the exterior surface of the housing. In other examples, the sensing unit is disposed underneath the display unit.

In one embodiment, blood pressure is determined by an application residing on the mobile device. Instructions comprising the application may further cause the processor to guide the user via the display unit to vary pressure being applied to the sensing unit while blood volume oscillations are measured. Instructions comprising the application may also cause the processor to guide the user to hold the mobile device at a height aligned with heart of the user.

DRAWINGS

The drawings described herein are for illustrative purposes only of selected embodiments and not all possible implementations, and are not intended to limit the scope of the present disclosure.

FIG. 1 is a diagram depicting an example embodiment of a mobile device that embodies cuff-less BP measurements;

FIG. 5 is a diagram depicting an example embodiment of the sensing unit;

FIG. 8 is a diagram depicting a prototype system that was created to test the feasibility of the oscillometric finger pressing paradigm;

FIGS. 17A-17C are diagrams depicting an embodiment of the cuff-less BP measurement system with finger placement indicators;

FIGS. 18A-18D are diagrams depicting an example position detection system included in the cuff-less BP measurement system.

Corresponding reference numerals indicate corresponding parts throughout the several views of the drawings.

DETAILED DESCRIPTION

Figure 2A:
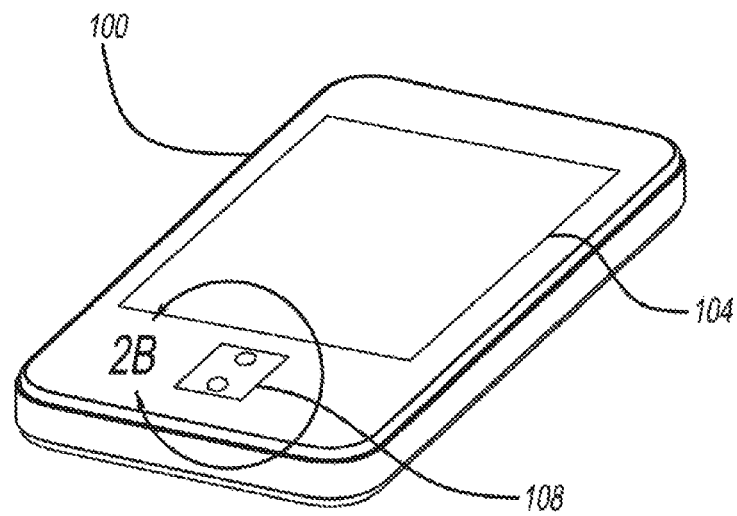
FIGS. 2A-2C are diagrams depicting an embodiment of the cuff-less blood measurement system on the mobile device.

Example embodiments will now be described more fully with reference to the accompanying drawings.

The present invention relates to a reliable method for cuff-less BP monitoring via the oscillometric principle. In conventional oscillometry, an inflatable cuff serves as both an actuator to vary the external pressure of an artery and a sensor to measure this pressure and the resulting variable-amplitude blood volume oscillations in the artery. BP is then estimated from the oscillation amplitudes as a function of the applied pressure (again, the "oscillogram"). The idea of this disclosure is to extend the oscillometric principle for cuff-less monitoring of BP using a smartphone, another mobile device (e.g., PDAs, laptops, tablets, and wearables), and/or possibly an encasing of a mobile device. Note that smartphones, in particular, are readily available even to those in low resource settings.

The user serves as the actuator by pressing her finger against the mobile device held at heart level to steadily increase the external pressure of the underlying artery. Such finger actuation may afford external pressure application similar to a cuff in that the artery will be pressed against supporting bone. The mobile device provides visual guidance for proper finger actuation, measures the applied pressure and blood volume oscillations, and estimates BP from the oscillogram. This invention could be implemented with a photoplethysmography (PPG) sensor, which measures pulsatile blood volume and a pressure sensor embedded in a smartphone encasing or within the phone itself. By having the user serve as the actuator, the requisite hardware is automatically miniaturized and greatly simplified. Note that the mobile device may also warn users of high BP, securely transmit the measured BP to caregivers, and send text reminders to patients with uncontrolled BP to take their medications. In this way, a complete hypertension management system would be available to many FIG. 1 is a diagram depicting an example embodiment of a cuff-less BP measurement system. The mobile device 100 includes a display 104 and a sensing unit 108. The display 104 may present graphics that depict, in a single graph 112, a pressure applied 116 by a finger to the sensing unit 108 over a target pressure 118 for the finger to exert, finger blood volume oscillations 120 from the sensing unit 108, as well as the SP, DP and MP of the user as indicated at 124 of the display. In an example embodiment, the user presses her fingertip against the sensing unit 108 to steadily increase the external pressure of the underlying artery, while the sensing unit 108, which includes a photoplethysmography (PPG) sensor and a pressure sensor, detects and measures the blood volume oscillations and the pressure applied 116 to the sensing unit 108. Using the measured blood volume oscillations 120 and the pressure applied 116 to the sensing unit 108, the oscillogram (i.e., amplitude of blood volume oscillations as a function of applied pressure) is generated. From the oscillogram, the SP, DP, and MP of the user are determined and presented, for example using a display of the device. In addition, the pressure applied 116 to the sensing unit 108 is displayed in the graph 112, and the blood volume oscillations 120 are displayed. The mobile device 100 includes but is not limited to mobile phones, PDAs, laptops, tablets, and wearable devices (e.g., watches).

Figure 2B:
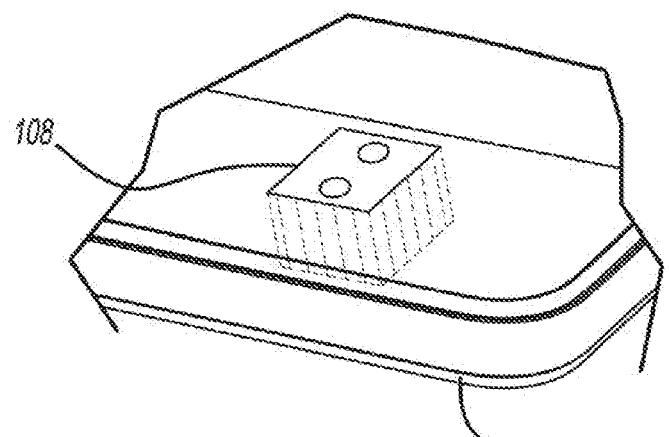
Figure 2C:
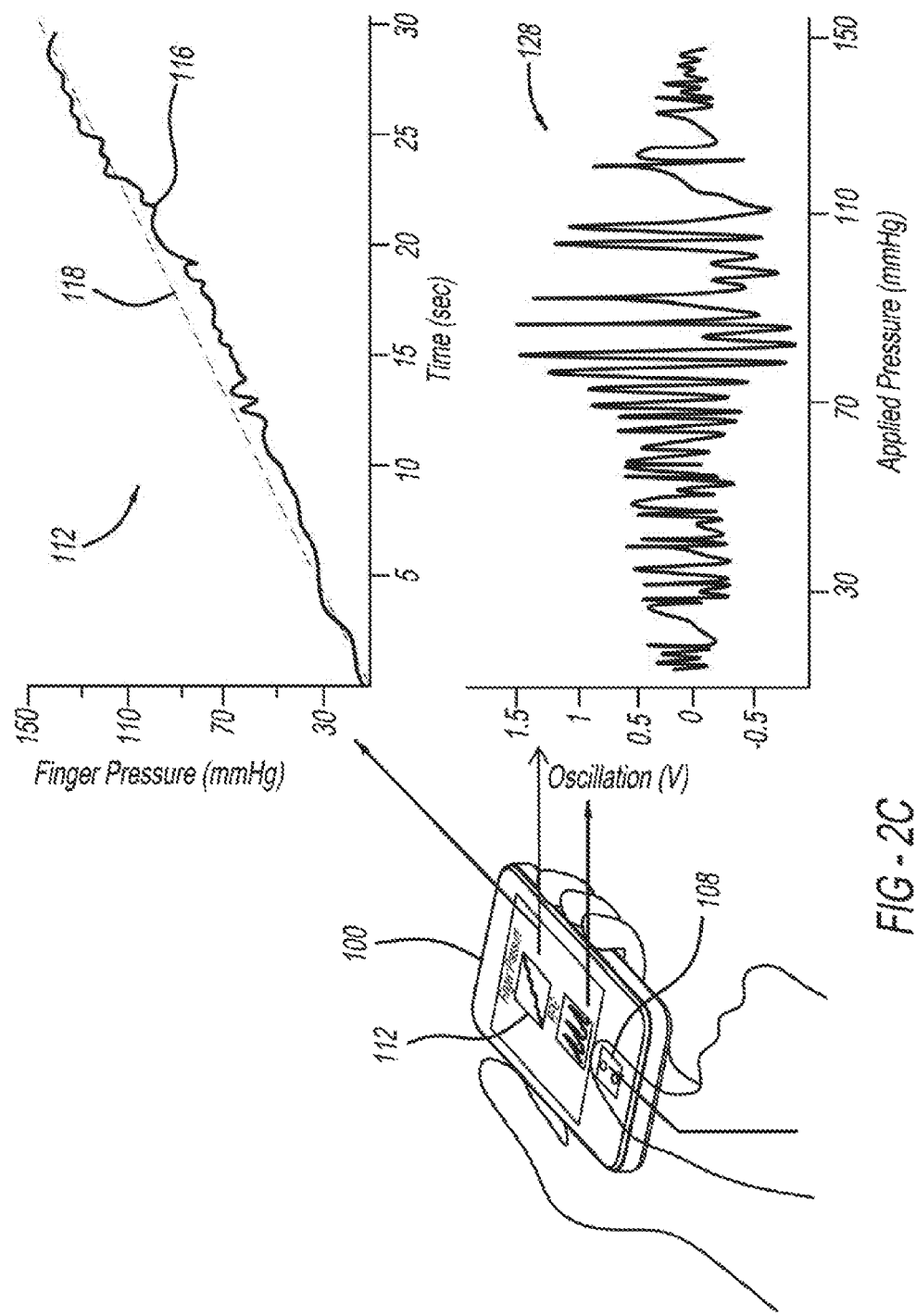

FIGS. 2A-2C are diagrams further depicting the embodiment of the cuff-less BP measurement system on the mobile device 100. The user serves as the actuator by pressing her finger against the mobile device 100, on the sensing unit 108, held at heart level to steadily increase the external pressure of the underlying artery. Finger actuation can afford external pressure application similar to a cuff in that the artery will be pressed against supporting bone.

The mobile device 100 provides visual guidance on the display 104 for proper finger actuation. That is, having the graph 112 of the pressure applied 116 to the sensing unit 108 on the same graph 112 as the target pressure 118 provides the user with visual feedback as to how much pressure to exert. The sensing unit 108 also measures blood volume oscillations 120 to generate an oscillogram 128, and BP is estimated from the oscillogram 128. The pressure applied 116 to the sensing unit 108 is graphed in relation to target pressure 118 to guide the user on the need to apply increased pressure and when to apply increased pressure. Graphing the pressure applied 116 to the sensing unit 108 in real time over the target pressure 118 allows the user to attempt to trace the target pressure 118. By having the user serve as the actuator, the requisite hardware is automatically miniaturized and greatly simplified. The SP, the DP, and the MP can be calculated from the oscillogram 128.

Figure 3:
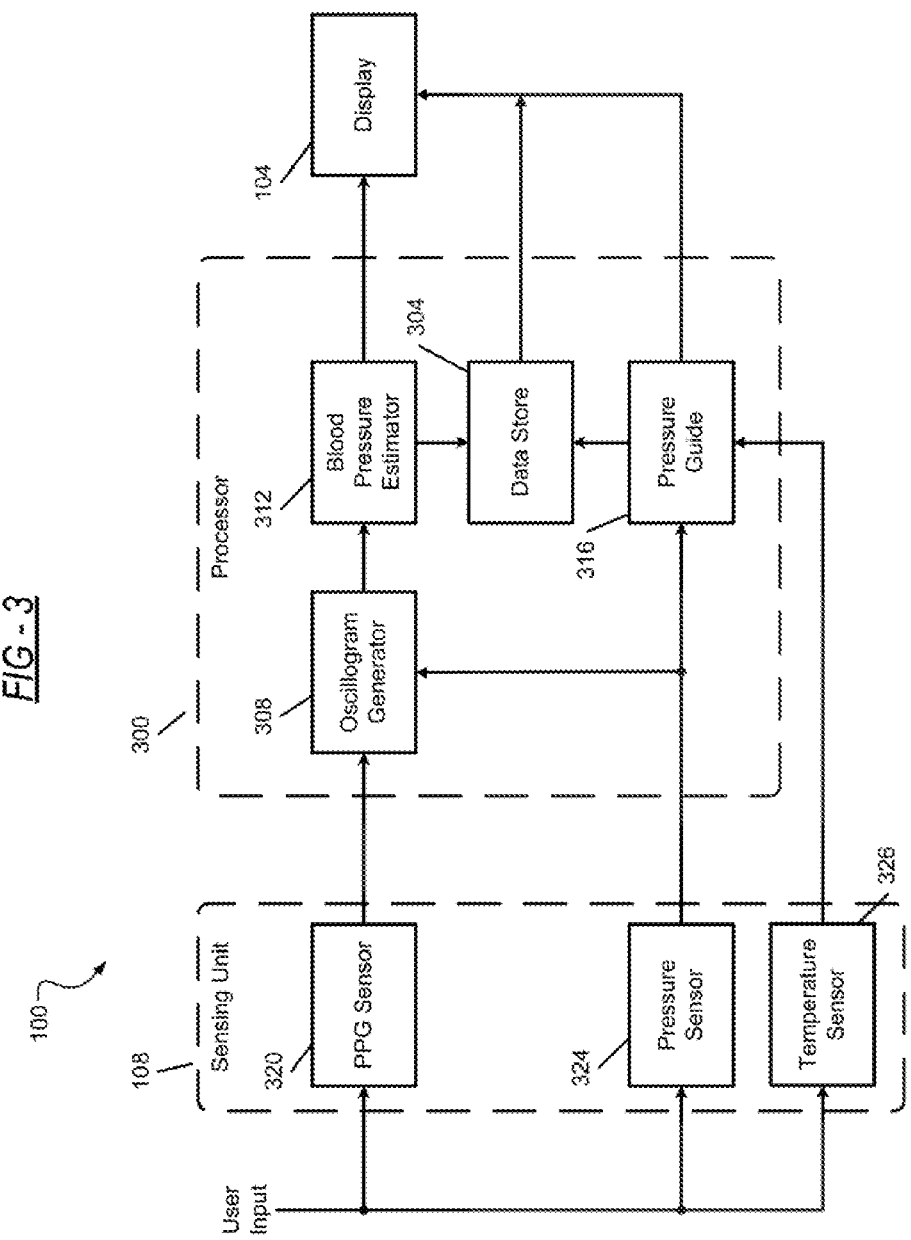
FIG. 3 is a diagram depicting an example embodiment of a cuff-less system in a mobile device that obtains BP measurements.

FIG. 3 is a diagram depicting an example embodiment of a cuff-less system that obtains BP measurements that may be implemented in the mobile device 100. The system includes a display 104, a sensing unit 108, a computer processor 300 and a data store 304 (e.g., a non-transitory storage medium). The system further includes an oscillogram generator 308, a BP estimator 312, and a pressure guide 316, which are implemented, for example, as computer-executable instructions residing in the data store 304 and executed by the computer processor 300.

The sensing unit 108 is operably coupled to the computer processor 300 of the mobile device 100. The sensing unit 108 includes a PPG sensor 320, a pressure sensor 324, and possibly a temperature sensor 326. The temperature sensor 326 is optional, and the BP measurements may be obtained without it. The PPG sensor 320 of the sensing unit 108 is operably coupled to the oscillogram generator 308, and the pressure sensor 324 is operably coupled to the oscillogram generator 308 and the pressure guide 30. The sensing unit 108 is configured to communicate the measured values of the PPG sensor 320 and the pressure sensor 324 to the computer processor 300 of the mobile device 100. An example embodiment of the sensing unit 108 is further described below in FIG. 5.

The oscillogram generator 308 is configured to generate an oscillogram based on input from the PPG sensor 320 and input from the pressure sensor 324. In an example embodiment, an oscillogram is constructed by first taking a maximum value and a minimum value of each beat of the blood volume waveform that is detected and measured by the PPG sensor 320. The maximum value and minimum value of each beat, as a function of the pressure applied 116 to the sensing unit 108 (obtained by the pressure sensor 324), are then median filtered to attenuate respiratory and heart rate variability. Finally, the maximum value and minimum value of each beat are linearly interpolated, and the difference between the two envelopes is taken as the oscillogram 128. Although not limited thereto, the oscillogram generator 308 may generate an oscillogram 128 using other known algorithms as would be understood by one having skill in the art.

In extending this algorithm of generating the oscillogram 128 using finger pressing instead of a cuff, issues of detecting beats in the presence of artifact and connecting the extrema of valid beats, which can be separated by a wide range of the pressure applied 116 to the sensing unit 108, may be present. To overcome these issues, algorithms that first identify artifact in the blood volume waveform that exploit the anticipated blood volume shape and then detect the maxima and minima of the artifact-free beats can be implemented into the system. Advanced filtering and splining algorithms, as well as parametric model (Gaussian functions) fitting, which may be more robust, can be used to connect the extrema of the clean beats.

To assess the validity of the oscillogram 128, various features such as the number of artifact-free beats, the applied pressure range over which these beats extend, and the shape, width, and degree of symmetry of the oscillogram 128 may be analyzed to determine the validity of the oscillogram 128. An algorithm such as linear discriminant analysis may be implemented to distinguish between valid and invalid oscillograms based on these features.

The BP estimator 312 is configured to determine the BP based on the oscillogram 128 generated by the oscillogram generator 308. Subsequently, the BP estimator 312 presents the BP value on the display 104. Example algorithms that may be used in estimating BP are the Standard Fixed-Ratio Algorithm, the Fixed-Slope Algorithm, a Patient-Specific Algorithm, and other variations of these algorithms. These algorithms may also be combined in various manners to estimate BP.

In addition, an age-dependent scaling algorithm of finger SP may be used to estimate brachial SP, since the ratio of finger SP to brachial SP may decrease with age. Brachial BP may also be determined from model-based transfer functions. While using the model-based transfer functions would require an input of the finger BP waveform, the finger BP waveform may be obtained using a Patient-Specific Algorithm. Some example embodiments of algorithms that may be used in estimating the BP are further described below in relation to FIGS. 6A-7B.

The pressure guide 316 may optionally be interfaced with the pressure sensor 324. In some embodiments, the pressure guide 316 scales the pressure applied to the pressure sensor 324 to a measure of pressure applied 116 to the sensing unit 108 exerted on the PPG sensor 320. The pressure guide 316 is also configured to present the estimated magnitude of the pressure applied to the sensing unit 108 on the display 104. By displaying the amount of pressure applied to the sensing unit 108 on the display 104, the pressure guide 316 also provides the user with real time feedback regarding the amount of pressure applied to the sensing unit 108 and the location of the finger relative to the sensing unit 108, as described further below. Thus, the user can take corrective action based on the real-time feedback so that the target pressure 118 can be applied to the sensing unit 108 for a predetermined period of time. The pressure guide 316 also receives feedback from the temperature sensor 326. The temperature sensor 326 measures a temperature of the finger applying pressure 116 to the sensor unit 108. Under the circumstance that the temperature of the finger is too low or possibly too high, the display provides feedback informing the user that the finger temperature is outside of an acceptable range, which can affect the results of the BP measurement system.

In an example embodiment, the oscillogram generator 308, BP estimator 312, and the pressure guide 316 may be implemented on the mobile device 100 as an application. The application can be used to guide the finger actuation, inform the user of any adjustments required in the pressure applied 116 to the sensing unit 108 or finger placement, graph finger pressure and possibly the blood volume oscillations 120, and display the graphs along with the SP, DP, and MP/BP. The application uses the display 104 and processor of the mobile device. For example, the application provides visual feedback to guide the finger actuation by graphing the pressure applied 116 to the sensing unit 108 over the target pressure 118. That is, the target pressure 118 may be a linear target rise or a pressure in step increments, which may yield more artifact-robust oscillograms over certain time interval (e.g., at least 15 sec). The pressure applied 116 to the sensing unit 108 is superimposed as it is being recorded in real-time. Alternatively, a display of the pressure applied 116 to the sensing unit 108 as it evolves in real-time within a plotting window that tells the user to raise the pressure steadily to a high level (e.g., 150 mmHg) over fixed time interval, but not in any preset way, may be used. A third option is to guide the finger actuation through a video game that requires the user press at various pressures to accomplish the goals of the game. In addition or in another embodiment, audio feedback could be used to guide the finger actuation.

Additionally, after the BP has been computed, the application may determine whether the BP is within an acceptable range. If the BP falls outside of the acceptable range, the application may instruct the user to repeat the BP measurement in order to ensure accuracy.

The application then displays the computed BP and other physiologic variables, if available, or asks the user to repeat the procedure in the event of an unsuccessful finger actuation. The application could also ask the user to repeat the procedure even when the actuation is deemed successful. For example, the application could average two similar BP measurements or the two closest BP measurements out of three total measurements to reduce variability. The application may also alert the user if the BP is too high or too low, securely transmit the measurements to the cloud as well as the physician, and send text reminders to users with repeatedly high BP measurements to take their medications. The application may further allow the user to view their history of BP measurements over time and integrate with other health and lifestyle applications on the mobile device 100 such as those that track eating habits.

The data store 304 is interfaced with the BP estimator 312 and the pressure guide 316. The data store 304 is configured to store BP values (MP, DP, and SP) that have been determined by the BP estimator 312. Pressure values from the pressure sensor 324 and PPG values from the PPG sensor 320 may also be stored in the data store 304. This may be useful for a user who is interested in tracking and analyzing BP values over a period of time to determine whether lifestyle changes, dietary changes, and/or exercise routines are improving her BP and overall cardiovascular health. The data store 304 may also be configured to provide the computer processor 300 of the mobile device 100 with processor readable instructions for the oscillogram generator 308, the pressure guide 316, and the BP estimator 312. As an example, the data store 304 may provide the computer processor 300 of the mobile device 100 with executable instructions that allow it to generate an oscillogram 128 from the blood volume oscillations detected and measured by the PPG sensor 320 and the pressure applied 116 to the sensing unit 108 detected and measured in the pressure sensor 324. The data store 304 may also provide the computer processor 300 of the mobile device 100 with executable instructions to estimate BP based on the oscillogram 128 generated by the oscillogram generator 308 and an algorithm that estimates BP based on certain parameters of the oscillogram 128.

The display 104 may provide the user with real-time feedback regarding the pressure applied 116 to the sensing unit 108 and the location of the finger relative to the sensing unit 108. As an example, the system may provide the user visual feedback when the pressure applied 116 to the sensing unit 108 is below a target pressure 118. As another example, the system may provide the user visual feedback when the location of the finger is not at a predefined optimal finger location that allows for optimal oscillogram measurements. The predefined finger location may be determined by an initialization protocol, which occurs when the finger actuation is attempted over a range of locations on the sensor, and the location that yields the largest oscillogram amplitude is selected as the predefined optimal finger location. The predefined optimal finger location may be located on the upper index finger above a transverse palmer arch artery of the subject.

To guide the user in increasing the pressure applied 116 to the sensing unit 108, the target pressure 118 may have a trajectory of a linear rise, a step increment, or a combination of a step increment and a linear rise shown on the display 104. In other embodiments, the target pressure 118 may not be displayed. For example, the display 104 could include the desired start and end pressures with the time interval to reach the end pressure.

Figure 4:
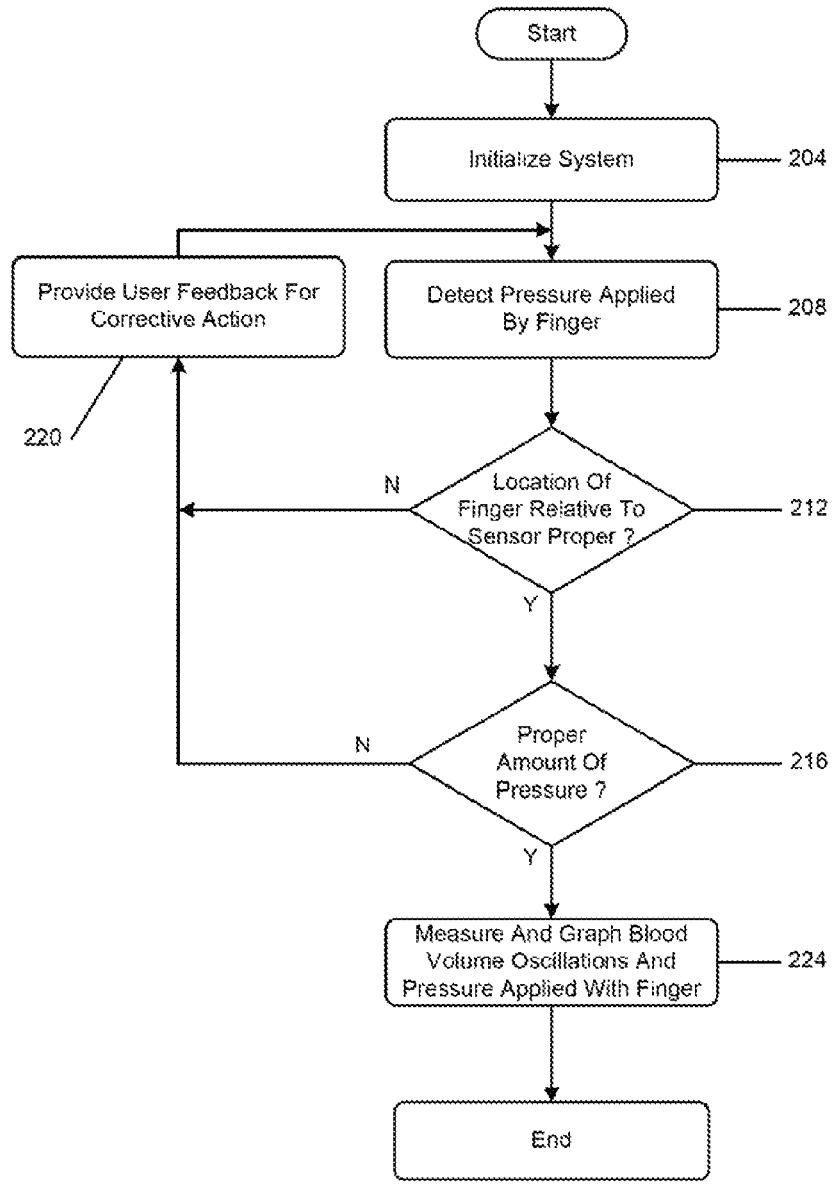
FIG. 4 is a flowchart depicting an example embodiment of a cuff-less system in a mobile device that obtains BP measurements.

FIG. 4 is a flowchart depicting an example embodiment of a cuff-less system that obtains BP measurements. The flowchart depicts an example of a determination of proper finger positioning and proper pressure applied 116 as may be implemented by the pressure guide 316 of FIG. 3. First, the system is initialized at 204. During this stage, the mobile device may initialize the display and the sensing unit (i.e., opening an application on the mobile device 100 and/or turning on the sensing unit 108) to measure the pressure applied 116 to the sensing unit 108, the blood volume oscillations 120 with the sensing unit 108, the oscillogram 128, and the SP, DP, and MP/BP and display the measurements once the user begins to apply pressure to the sensing unit 108. The mobile device 100 may also, using information loaded in a data storage unit, load the user's predefined optimal finger location data. The user data may be accessed by the initialization protocol by inserting a username or ID and a password to load the user's predefined optimal finger location data.

Second, the system begins to detect the pressure applied 116 to the sensing unit 108 at 208. Next, the system provides the user with real-time feedback. At 212 the system then determines whether the location of the finger relative to the sensor is proper, wherein the proper location is the predefined optimal finger location. If so, then at 216 the system determines whether the user is applying the proper amount of pressure, wherein the proper amount of pressure is the target pressure 118. If so, the system proceeds to the next step.

If the location of the finger relative to the sensing unit 108 is not proper at 212, or if the amount of pressure is not proper at 216, the system, at 220, provides corrective feedback so that the user can either correct the amount of pressure applied to the sensing unit 108 or adjust her finger positioning relative to the sensing unit 108. As an example, the feedback may instruct the user to either increase or decrease the amount of pressure applied so that the user can apply the target pressure 118. As another example, the feedback may instruct the user to adjust the positioning of her finger so that the positioning of the finger is at the predefined optimal finger location. Control then proceeds to 208. The feedback may be visual, audio-based, or a combination of visual and audio-based feedback.

Once the target pressure 118 is met and proper finger positioning is achieved, the sensing unit 108 measures and graphs the blood volume oscillations and the pressure applied 116 to the sensing unit 108 at 224. The system then displays the BP to the user. The system determines the SP and DP based on the blood volume oscillations and the pressure applied 116 to the sensing unit 108. Using the SP and DP, the system estimates the MP/BP from the blood volume oscillations and the pressure applied 116 to the sensing unit 108 using various BP estimation algorithms. Depending on the determination method, the MP/BP may be determined first followed by the SP and DP. In any case, the mobile device 100 subsequently displays the MP/BP.

FIG. 5 is a diagram depicting an example embodiment of the sensing unit 108. The sensing unit 108 includes a PPG sensor 320 and a pressure sensor 324, wherein the PPG sensor 320 and the pressure sensor 324 are coupled to each other by an interface unit 328. The PPG sensor 320 and the pressure sensor 324 may be coupled to the computer processor 300 of the mobile device 100, wherein the computer processor 300 of the mobile device 100 may subsequently determine the BP from the detected values of the PPG sensor 320 and the pressure sensor 324. The sensing unit 320 surface may be flat or concave to facilitate finger positioning on the sensing unit 108.

In an example embodiment, the PPG sensor 320 is an infrared, reflectance-mode PPG sensor that measures blood volume oscillations from the arteries beneath the skin. The PPG sensor 320 may be configured in a way such that the blood volume oscillations of a transverse palmer arch artery, above the top knuckle of the index finger, can be accurately and efficiently recorded. An LED and a photodetector (referenced and discussed in FIG. 13) of the PPG sensor 320 may be positioned perpendicular to the transverse palmer arch artery, wherein the LED and the photodetector are separated by a fixed distance. The fixed distance may be chosen such that the blood volume oscillation amplitudes detected and measured by the PPG sensor 320 are maximized.

In an example embodiment, the pressure sensor 324 is a thin-filmed capacitive transducer. The transducer outputs the pressure applied 116 to the sensing unit 108 in the normal direction. The pressure sensor 324 may be configured to output a pressure between the range of 0 to 250 mmHg at an output resolution of less than 0.1 mmHg. Other pressure sensors that are configured to output a force when the pressure applied 116 to the sensing unit 108 may also be used instead of the thin-filmed capacitive pressure sensor 324 described in this embodiment.

In an example embodiment, the interface unit 328 is a thin, rigid structure 328A adhesively coupled to a foam material 328B. The rigid structure of the interface unit 328A is coupled to the PPG sensor 320, while the foam material of the interface unit 328B is coupled to the pressure sensor 324. This interface unit 328 allows for the force applied to the PPG sensor 320 to be distributed uniformly to the pressure sensor 324.

Alternatively, a silicone layer or similar material may be used in place of the foam material 328B. Other materials that may be used in place of the foam material 328B are materials that are configured to distribute an applied force evenly over its respective area and acts as a mechanical low-pass filter to mitigate the impact of any spurious finger pressing.

A surface of the sensing unit 108 that receives the pressure applied 116 to the sensing unit 108 from the user should have an area that is optimized in order to allow for reliable BP estimation. For example, in certain embodiments, if the area of the surface is too large, then substantial force will be needed to achieve the target pressure 118. If the area of the surface is too small, then modest variations in pressure applied 116 to the sensing unit 108 will induce substantial pressure changes. The area of the surface of the sensing unit 108 that receives the applied force from the subject should therefore be optimized to allow for the sensing unit 108 to measure and detect the pressure applied 116 to the sensing unit 108 that achieves an optimal balance between these two considerations.

Figure 6A:
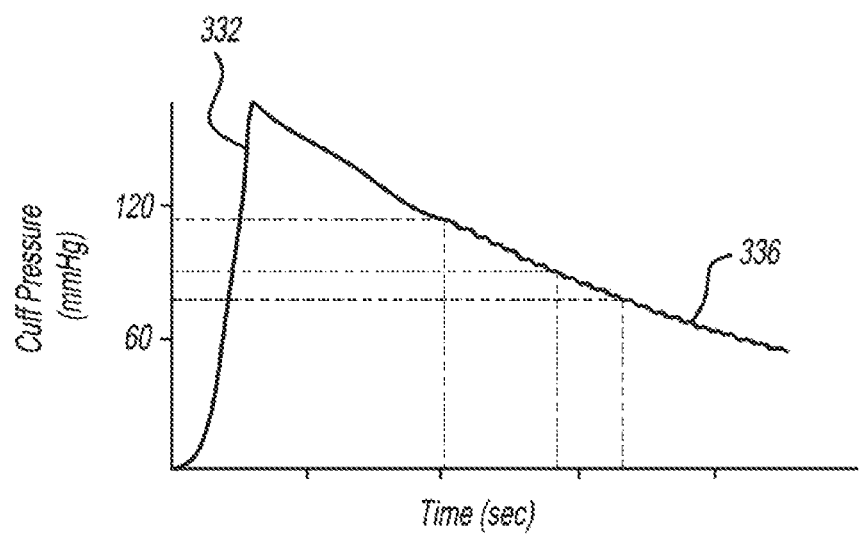
FIGS. 6A and 6B are an example embodiment of how BP is estimated using a Standard Fixed-Ratio Algorithm.
Figure 6B:
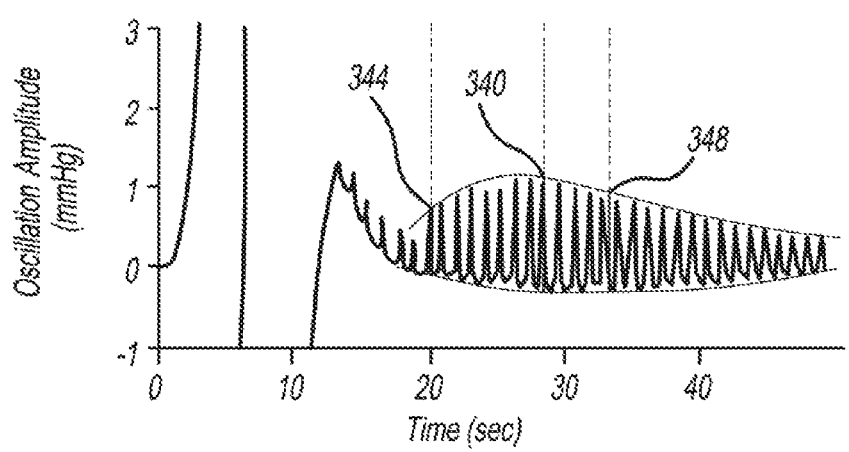

FIGS. 6A and 6B are an example embodiment of how BP is estimated using a Standard Fixed-Ratio Algorithm. As described above, the oscillogram generator 308 receives data from the PPG sensor 320 and the pressure sensor 324

(e.g., the pressure applied 116 as depicted in FIG. 6A at 332 and 336) to generate an oscillogram.

FIG. 6A is a diagram depicting the pressure applied 116 to an artery. A cuff is placed around a patient's arm and inflated. The cuff is inflated while secured around the patient's arm, shown in FIG. 6A where the cuff pressure is increasing rapidly 332. Once the cuff reaches a target external pressure to the artery, the cuff slowly deflates 336. While deflating 336, the cuff measures a blood volume value and external pressure and constructs an oscillogram from the resulting variable amplitude blood volume oscillations shown in FIG. 6B. The mean BP (MP) 340 is estimated as the pressure at which the oscillogram is at a maximum amplitude 340 ($A_M$). Then, an amplitude of the SP ($A_S$) 344 and an amplitude of the ($A_D$) DP 348 are estimated as the pressure at which the oscillogram is a fixed, population based average ratio of its maximal value ($A_S/A_M$ and $A_D/A_M$). The ratios in this embodiment are fixed such that $A_S/A_M$ and $A_D/A_M$ are equal to 0.55 and 0.85, respectively. While this method depicts measuring BP using the cuff, this algorithm can be applied in a cuff-less system as well, wherein finger pressure is used instead of cuff pressure.

However, since the Standard Fixed-Ratio Algorithm is population based, the algorithm may be less effective in accurately determining BP levels for those individuals who have BP not within a normal BP range. The BP estimation errors of the Standard Fixed-Ratio Algorithm may be significant and may be impacted by the width of the arterial compliance curve, which is the derivative of the blood volume transmural pressure relationship with respect to transmural pressure. The accuracy of the Standard Fixed-Ratio Algorithm may also be affected by those who have a high pulse pressure (i.e., the difference between the SP and DP) due to artery stiffening, a common condition that occurs with aging and disease.

Figure 7A:
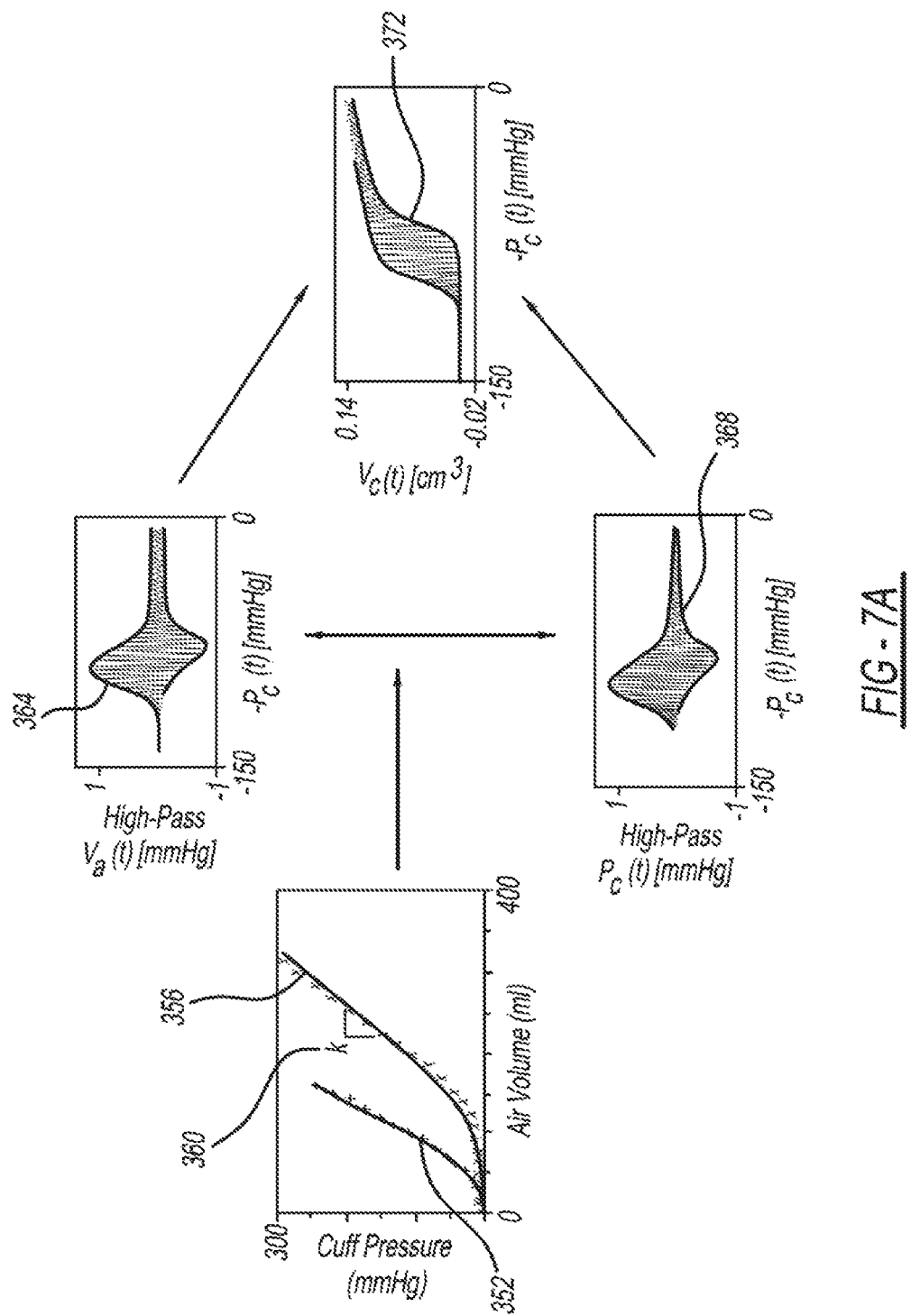
FIGS. 7A and 7B are diagrams depicting an example embodiment of how BP is estimated using a Patient-Specific Algorithm.
Figure 7B:
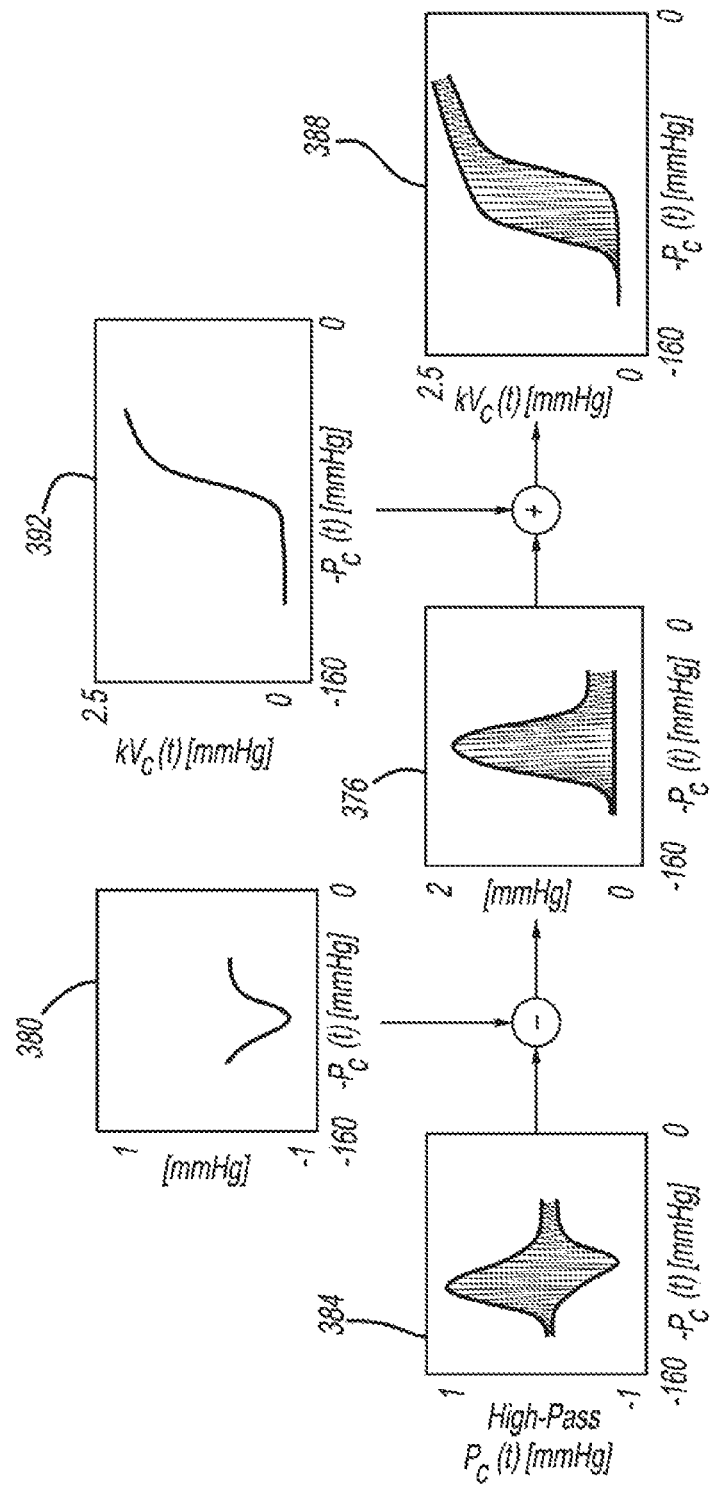

FIGS. 7A-7B are diagrams depicting an example embodiment of how BP is estimated using a Patient-Specific Algorithm. The oscillograms depicted at 368, and 384 are produced by the oscillogram generator 308 described in FIGS. 3. The Patient-Specific Algorithm represents the oscillogram 128 with a physiologic model and then estimates the patient-specific model parameters, which include BP levels and reflect the width and other features of the arterial compliance curve by optimally fitting the model to the oscillogram 128. Thus, accuracy can be maintained over a wide BP range. Furthermore, by employing a physiologic model, the method can be more robust to deviations in the oscillogram 128 caused by respiration and heart rate variability and thus be more repeatable and reliable. While this method depicts measuring BP using a cuff, this algorithm can be applied in a cuff-less system as well, wherein finger pressure is used instead of cuff pressure.

In FIG. 7A, air volume versus cuff pressure is shown for two different types of cuffs: a dura cuff 352 and a bladder cuff 356. From the nearly linear relationship displayed in FIG. 7A, a cuff compliance or scale factor k 360 is determined.

The first step of estimating BP using the Patient-Specific Algorithm is to represent the cuff pressure oscillation amplitude versus the cuff pressure function (i.e., the oscillogram) with a parametric model of the nonlinear brachial artery blood volume-transmural pressure relationship. This representation is demonstrated in the following equation 1:

$$\underbrace{P_c^{oa}(t)}_{\text{Red Envelope Difference}} = \frac{e}{k \cdot d} \underbrace{\left\{1 + \left[b^{-1}\left((SP - P_c(t) - a) + b\left(\frac{c-1}{c+1}\right)^{1/c}\right)\right]^{-c}\right\}^{-1}}_{\text{Nonlinear relationship at systole}} -$$

-continued $$e\underbrace{\left\{1 + \left[b^{-1}\left((DP - P_c(t) - a) + b\left(\frac{c-1}{c+1}\right)^{1/c}\right)\right]^{-c}\right\}^{-1}}_{\text{Nonlinear relationship at diastole}}$$

The unknown parameters (a, b, c, and e) represent the SP, DP, and brachial artery mechanics. In terms of the brachial artery compliance curve (i.e., the derivative of the nonlinear relationship with respect to transmural pressure), parameter a represents the transmural pressure at which the curve is a maximum; parameters b and c denote the width of the curve and the extent of the asymmetry about its maximum; and parameter e indicates the amplitude of the curve. The parameter e is determined by the reciprocal of the cuff compliance, which is represented by scale factor k 360. The scale factor k 360 is assumed to be constant as justified by experimental data. A blood volume 372 is determined based on (i) the nearly linear relationship of the cuff pressure and air volume 356, (ii) blood volume oscillations 364, and (ii) cuff pressure oscillations 368. The envelope differences of the blood volume 372 are equal to within scale factor k 360.

The second step of estimating BP using the Patient-Specific Algorithm is to estimate the model parameters including the SP and DP by fitting the model to the oscillogram. The model parameters are estimated using the following equation 2:

$$\min_{\{a,b,c,e,SP,DP\}} \sum_{t \in \text{Deflation} \atop \text{Period}} \left[ P_c^{oa}(t) - \right.$$

$$e\left\{1 + \left[b^{-1}\left((SP - P_c(t) - a) + b\left(\frac{c-1}{c+1}\right)^{1/c}\right)\right]^{-c}\right\}^{-1} +$$

$$\left. e\left\{1 + \left[b^{-1}\left((DP - P_c(t) - a) + b\left(\frac{c-1}{c+1}\right)^{1/c}\right)\right]^{-c}\right\}^{-1}\right]^2$$

The first step and the second step yield estimates for SP and DP as well as parameters a, b, c, and e, which characterize the underlying model of the nonlinear brachial artery blood-volume transmural pressure relationship. The third and fourth step use the parameter estimates to ultimately yield an estimate for the entire brachial BP waveform ($P_b(t)$) and MP, as described next.

The third step of estimating BP using the Patient-Specific Algorithm, which is shown in FIG. 7B, is to construct the blood volume waveform to within the scale factor k 360 using the parameter estimates (i.e., a, b, c, and e) and cuff pressure oscillations. Positive cuff pressure oscillations 376 are calculated by subtracting a lower cuff pressure oscillation envelope 380 from cuff pressure oscillations 384. Then, the blood volume waveform to within scale factor k 388 is calculated by adding a modeled arterial blood volume-transmural pressure relationship at diastole to within scale factor k 392.

The fourth step of estimating BP using the Patient-Specific Algorithm is to construct the BP waveform using the blood volume waveform 388 via root finding. From the BP waveform, MP is computed as the time average of the derived waveform. The following equation 3 illustrates how the BP waveform and the MP are derived:

$$k \cdot V_a(t) = e \left\{ 1 + \left[ b^{-1} \left( (P_a(t) - P_c(t) - a) + b \left( \frac{c-1}{c+1} \right)^{1/c} \right) \right]^{-c} \right\}^{-1}$$

Further details regarding the Patient-Specific Algorithm may be found in U.S. Provisional Application No. 62/217,331 filed Sep. 11, 2015 incorporated by reference in its entirety herein.

The oscillometric principles of an inflatable cuff as described in FIGS. 6A-7B are applied to cuff-less BP monitoring as shown in a prototype system 394. FIG. 8 is a diagram depicting the prototype system 394 that was created to test the feasibility of the oscillometric finger pressing paradigm.

Figure 9A:
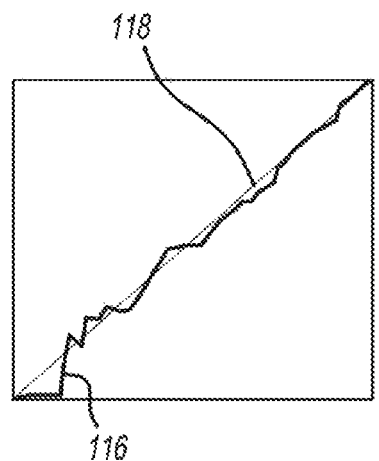
FIGS. 9A and 9B are graphs depicting the pressure applied to the sensing unit and the target pressure displayed when pressure is applied to the sensing unit as well as the oscillogram that is generated to determine BP.
Figure 9B:
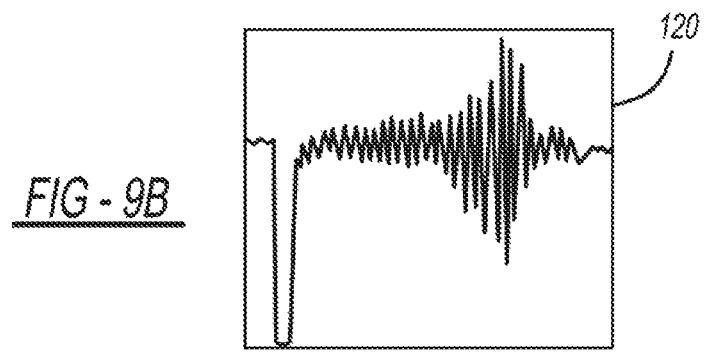

The prototype system 394 consists of a simple sensor unit interfaced to a computer, which provides a visual display, as shown in FIGS. 9A and 9B, and runs standard algorithms to estimate BP.

The sensing unit includes the PPG sensor 320 and pressure transducers as the pressure sensor 324 housed in a plastic enclosure. The PPG sensor 320 is an LED and photodetector operating in reflectance-mode and at an infrared wavelength (940 nm) to penetrate an artery beneath the skin. The PPG sensor 320 surface, which constitutes the finger pressing area, is a 10 mm diameter circle. The pressure sensor 324 (DigiTacts Sensors, Pressure Profiling Systems, USA) is a thin-filmed, 16×3 array of capacitive transducer elements (5 mm length squares). Each element outputs the pressure exerted on it in the normal direction and has specifications that are congruent with BP measurement (e.g., resolution and range are <1 mmHg and >250 mmHg). The PPG sensor 320 is on top of the pressure sensor 324 with a rigid structure-foam sheet interface between the two. This interface allows the force applied on the PPG sensor 320 (but not elsewhere on the enclosure) to reach the pressure sensor 324 and be uniformly distributed on the pressure sensor 324. The applied finger pressure is the total force measured by all of the sensing elements divided by the pressing area. The pressure sensor 324 was calibrated as it resides in the sensing unit by placing high density weights on the PPG sensor 320. The relationship between the measured voltage and known pressure was nearly linear over physiologic pressures.

FIGS. 9A and 9B are graphs depicting the pressure applied 116 to the sensing unit 108 and the target pressure 118 displayed when pressure is applied to the sensing unit 108 as well as the blood volume oscillations 120 that are also generated to determine BP. The sensing unit is connected to the computer via a data acquisition system (NI USB6009, National Instruments, USA). The visual display, which is implemented using the data acquisition system software (LabVIEW, National Instruments), guides the user in performing the finger actuation. The guidance is simply a display of the applied finger pressure 116 as it evolves in real-time within a plotting window that tells the user to raise the pressure steadily to 150 mmHg over a 30-sec interval but not in any preset way (e.g., a linear rise). The display also illustrates the blood volume oscillations 120 as it is being measured and estimated BP levels. Standard algorithms, which are implemented using computing software (MATLAB, Mathworks, USA), are applied to the measured finger pressure 116 and the blood volume oscillations 120 to construct an oscillogram 128 and estimate finger BP. In particular, BP is estimated using the fixed-ratio algorithm with the ratios set to typical values of 0.85 for DP and 0.55 for SP.

Figure 10:
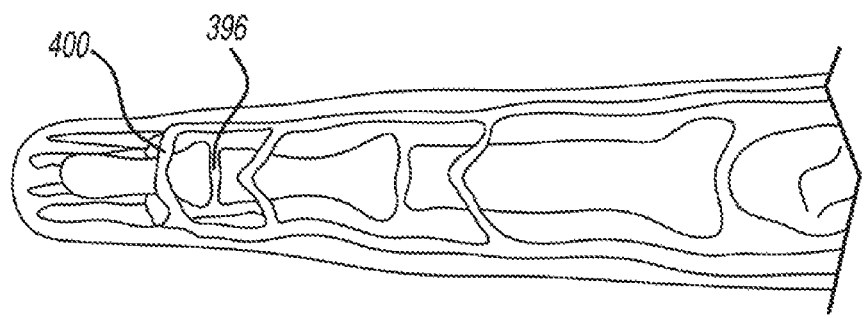
FIG. 10 is a diagram depicting an index finger that exerts the pressure applied to the sensing unit of the prototype system.

FIG. 10 is a diagram depicting an index finger that exerts the pressure applied 116 to the prototype system 394. The finger pressing protocol includes pressing the PPG sensor 320 with the center of the index finger, shown in FIG. 10, above the top knuckle 396, which is above the transverse palmer arch artery 400. The protocol further includes instructing the user to apply the force in the normal direction while the finger is at heart level in order to eliminate confounding hydrostatic effects. As previously described, the user may follow the finger pressing protocol through the display 104 of the mobile device 100 using an application to display the necessary graphs and prompts on the display 104. When measuring the BP of the index finger, the traverse palmer arch artery 400 is the target artery, as discussed below.

Figure 11:
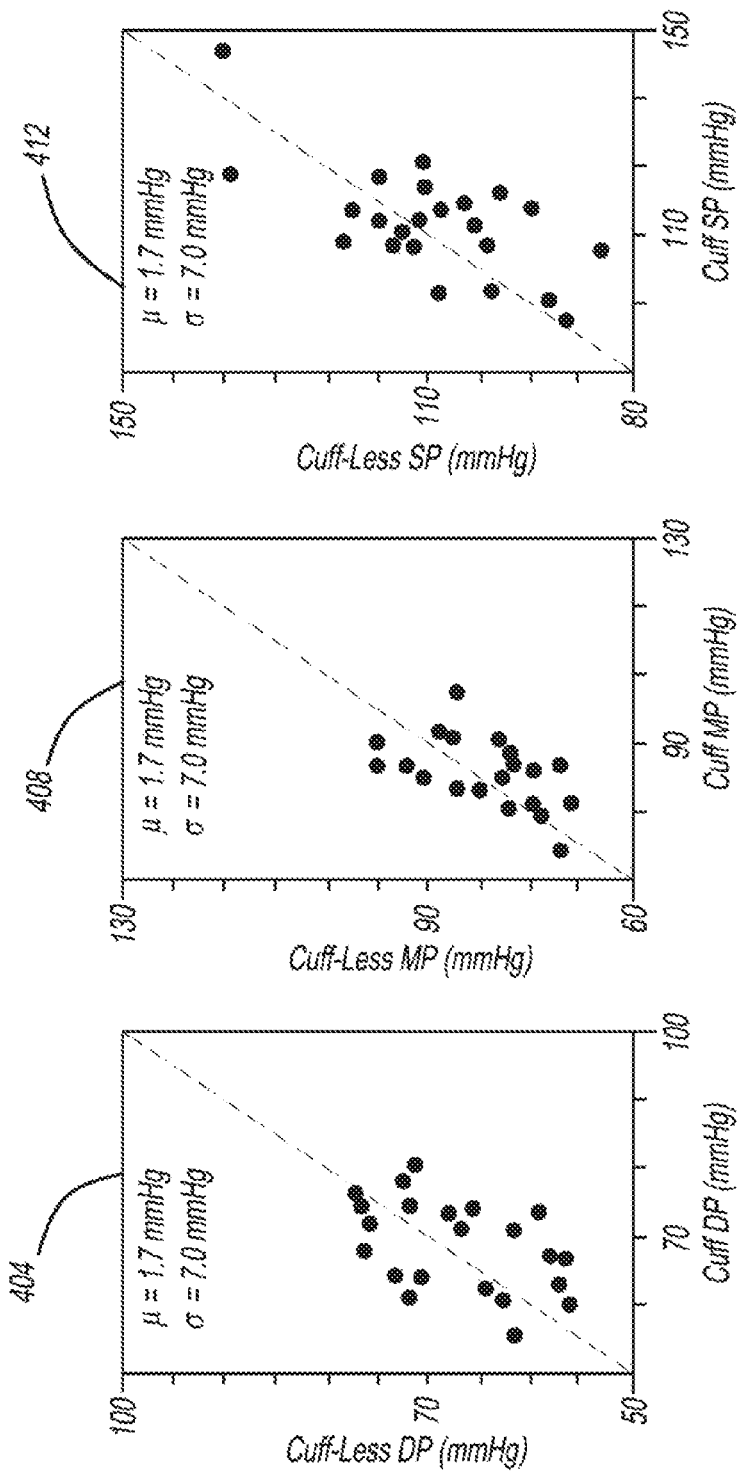
FIGS. 11A-11C are diagrams depicting results of testing a prototype system.

FIGS. 11A-11C are diagrams depicting the results of the prototype system 394. This basic prototype system 394 was studied in human subjects in the seated posture (similar to cuff BP measurements) under IRB approval. Each subject addressed the sensing unit placed on a table at heart level to eliminate hydrostatic effects. The subject placed the center of her index finger above the top knuckle 396 on the center of the PPG sensor 320. In this way, BP from the transverse palmer arch artery 400 would be targeted for measurement. The subject also rested a portion of her finger below the top knuckle 396 on the sensing unit enclosure to ensure normal direction force application. The subject then performed the finger actuation under visual guidance. Many people, including those in their 60's, could easily implement the finger actuation on the first try or after one or two practice trials.

The cuff-less BP estimates of the system were compared to BP measurements from an oscillometric arm cuff device (BP760, Omron) in 23 mostly inexperienced students and staff at Michigan State University (MSU). Each subject was allowed to practice the finger actuation a couple of times before recording the BP estimates. FIGS. 11A-11C depict cuff-less BP estimates versus the cuff measurements. FIG. 11A depicts the cuff-less DP versus the cuff DP 404. FIG. 11B depicts the cuff-less MP versus the cuff MP 408. FIG. 11C depicts the cuff-less SP versus the cuff SP 412. The bias and precision errors were about 1-3 and 7-11 mmHg. Since finger SP is larger than brachial SP, a crude estimate of brachial SP via a basic formula (SP=2.5*MP−1.5*DP) was instead used here.

Figure 12:
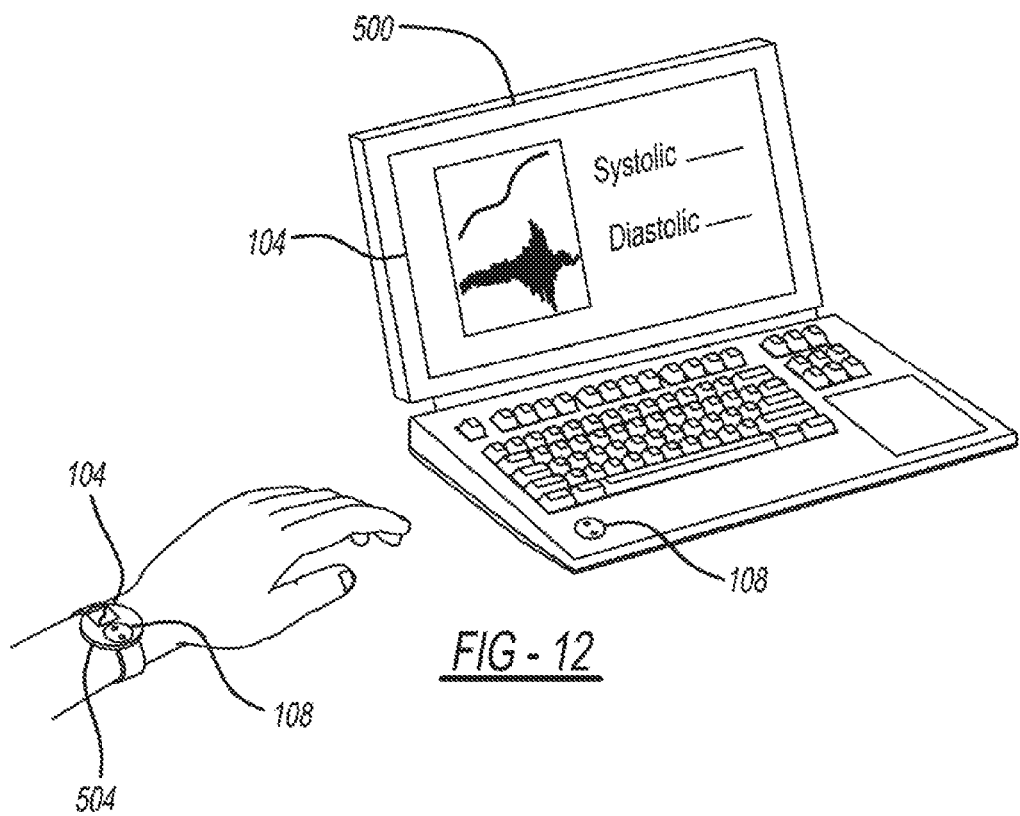
FIG. 12 is a diagram depicting an example embodiment of cuff-less BP measurement devices.

FIG. 12 is a diagram depicting an example embodiment of cuff-less BP measurement devices. FIG. 12 depicts the measurement system included in a computer 500 and a watch 504. The computer 500 and the watch 504 include the sensing unit 108 and the display 104 as shown in FIG. 1.

Figure 13:
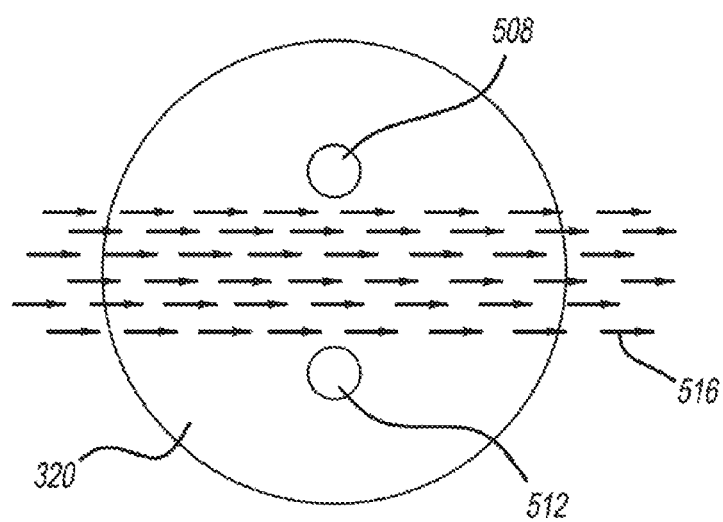
FIG. 13 is a diagram depicting an example PPG sensor on the sensing unit.

FIG. 13 is a diagram depicting an example PPG sensor 320 on the sensing unit 108. To measure the blood volume oscillations, any available sensor known in the art may be employed. As shown in FIG. 13, the PPG sensor 320, which is implemented in pulse oximeters, is used. The reflectance-mode PPG sensor, in particular, may be congruent with most form factors. The green wavelength, which typically yields a high AC signal relative to the DC signal, or a near infrared wavelength, which penetrates beneath the skin, or multiple wavelengths (e.g., red and infrared to also permit measurement of arterial oxygen saturation (SpO2)) may be employed.

A single photodetector 508 and light emitting diode 512 (LED) pair may be used for measurement of blood volume in a target artery 516 such as the transverse palmer arch artery 400 above the top knuckle 396 of an index finger (see FIG. 10). The distance between the LED 512 and photodetector 508 may be a few (e.g., 2) millimeters and positioned in various ways including on a line perpendicular to the flow of arterial blood, as shown in FIG. 13. The arrows of the target artery 516 depict the arterial blood flow.

Alternatively, the PPG sensor 320 may be transmissive-mode PPG. For example, the PPG sensor 320 can be in a ring or "clothespin" format with the pressure sensor mounted below the photodetector 508. When the user presses their finger or thumb inside the PPG sensor 320 ring onto an external, hard surface, the finger deforms. The ring can be made out of a soft material to enable the proper transmission of the force and keep the LED 512 preloaded onto the top of the finger.

Figure 14:
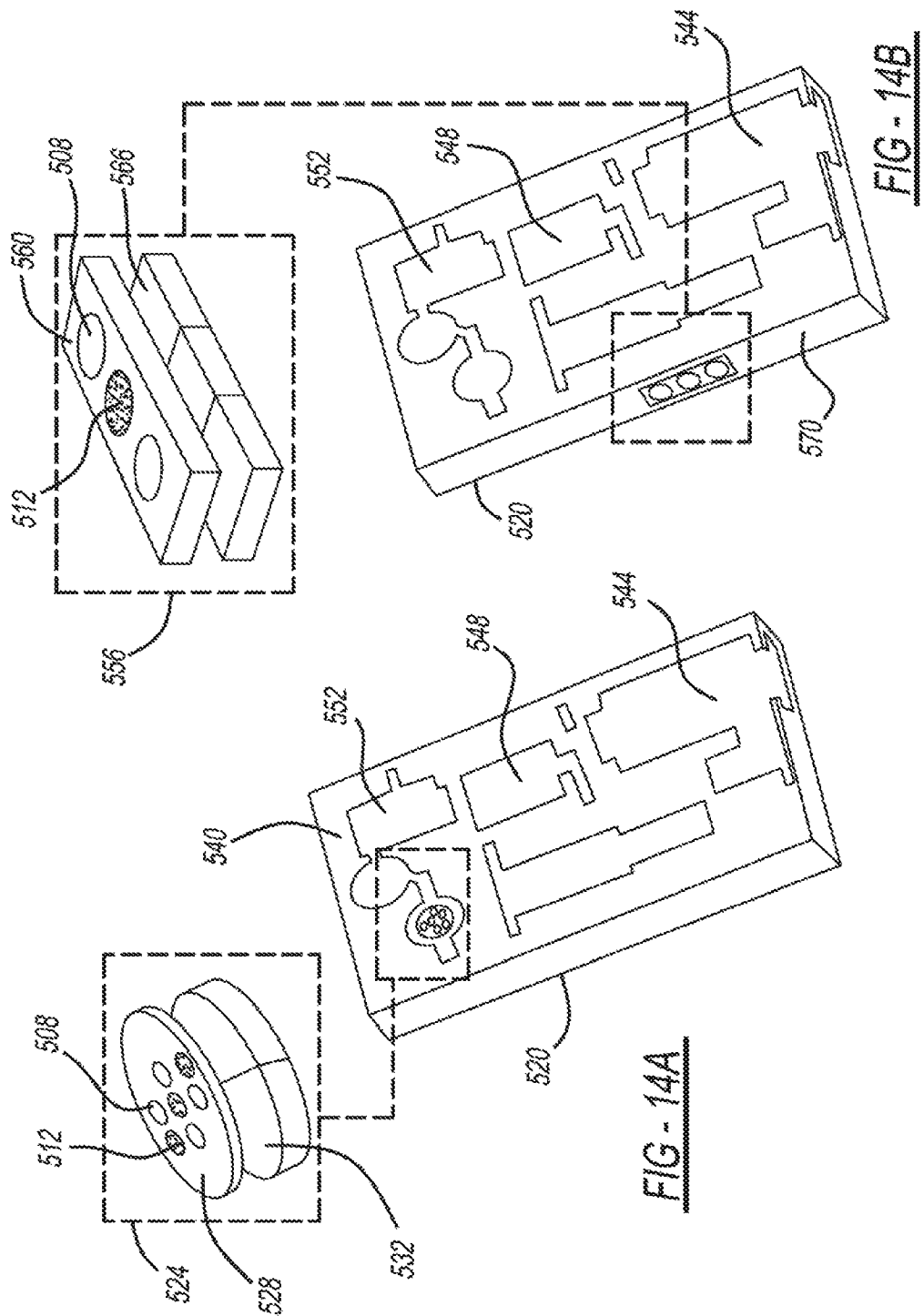
FIGS. 14A and 14B are diagrams depicting example embodiments of sensing units coupled to an encasing of mobile devices.

FIGS. 14A and 14B are diagrams depicting example embodiments of sensing units integrated into an encasing 520 of mobile devices 100. The encasing 520 of the mobile device 100 is a sleeve designed to enclose the mobile device 100. Cases are commonly used for mobile devices 100 to protect the mobile device 100 from damage such as scratches. In the present disclosure, the encasing 520 is a separate sleeve for the mobile device 100 and includes the necessary components for the BP measurement system. The encasing 520 is designed to interface with the mobile device 100 using a network communication device such as Bluetooth.

In FIG. 14A, a circular sensing unit 524 is shown. The circular sensing unit 524 includes a PPG sensor array 528 with multiple light emitting diodes (LEDs) 512 and multiple of photodetectors 508. The PPG sensor array 528 is coupled to a pressure array 532. Alternatively, a single LED 512 may be employed, as exemplified in FIG. 14B. With the PPG sensor array 528, the target artery 516 may be located and blood volume oscillations from therein may be measured via selection of the largest amplitude waveform obtained from the photodetectors 508. The surface of the PPG sensor array 528, which constitutes the finger pressing area, may be circular with a 10 mm diameter or occupy a similar area with the same or different shape, such as a rectangle 536, as shown in FIG. 14B. The 10 mm area facilitates the finger actuation in that a high enough pressure can be easily achieved without being overly sensitive to the finger forces. The PPG sensor array 528 surface may be flat or concave to facilitate finger positioning on the PPG sensor array 528.

In another embodiment, a red, green, and blue (RGB) camera (e.g. from e-con Systems, USA) can be used as reflectance-mode PPG sensor array. The RGB camera can operate as multiple photodetectors and the camera flash can operate as a light source. Each pixel in a RGB video provides blood volume waveforms at the three wavelengths. That is, the RGB video can construct a "PPG image". From the PPG image, "hot spots" in the finger can be identified to measure the blood volume from the target artery 516. The RBG camera, already built in the mobile device, may be leveraged to measure the blood volume oscillations.

FIG. 14A also depicts the PPG sensor array 528 as coupled to the pressure array 532. Various pressure or force sensors such as resistive, capacitive, or piezoelectric transducers may be included in the pressure array 532 to measure the pressure applied 116 to the sensing unit 108. The specifications for the pressure sensor should be congruent with the measurement of BP (e.g., a pressure range of 0 to 300 mmHg and a resolution of about 0.1 mmHg). As discussed above, the pressure sensor may be thin-filmed. In other embodiments, larger sensors such as load cells could be accommodated in certain form factors. The pressure sensor array 532 would typically be the same size as the PPG sensor array 528 surface. A single pressure transducer may be employed or multiple, smaller pressure sensing elements could be used to ensure that the pressure is being uniformly applied via examination of the similarity amongst the forces exerted on each individual sensor. In other words, one of the benefits of using multiple pressure sensors, in any array form, is that the force applied to each individual pressure sensor can be measured to determine whether the force is applied uniformly on the pressure sensors. That is, if the forces applied to each pressure sensor vary amongst one another, the force is not being applied uniformly. The force applied to each pressure sensor can be used to guide a user for successful actuation of the sensor.

As shown in FIG. 14A, the circular sensing unit 524 is embedded on a back 540 of an encasing 520 for the mobile device 100. The encasing 520 includes a processor 544, a battery 548, and an analog to digital converter 552. The encasing 520 may include a data acquisition system to record measurements of BP in storage already included on the mobile device the encasing 520 holds. The system would include analog signal conditioning (including signal amplification and filtering with, e.g., low and high cutoff frequencies of about 0.5 to at least 10 Hz) followed by analog-to-digital conversion at 552 (with, e.g., a sampling rate of at least 25 Hz and a resolution of 12 bits or more). Alternative to the processor 544 a microcontroller may be included in the encasing 520. The microcontroller may include a Bluetooth transmission module, which may be employed to send the digitized data wirelessly to the mobile device 100 for display and processing. In other embodiments, any network communication device may be used to receive and transmit digitized data between the encasing 520 and the mobile device 100.

The entire "external" system may be battery powered by the battery 548. In form factors built into the mobile device, the digitized data may be sent to the display 104 and stored in an available medium for processing in the mobile device 100. The storage medium, however, may be included in the encasing 520. The necessary components could also be added on to or included in existing mobile devices 100 such as a cell phone, PDAs, laptops, tablets, wearables including smartwatches and wristbands, or any other form of a portable electronic device.

To compute BP or determine that the finger actuation was unsuccessful, the recorded data, stored in the storage medium, are analyzed by a set of algorithms implemented on the mobile device's processor 544.

The quality of the pressure applied 116 to the sensing unit 108, e.g., in FIG. 9A, and blood volume waveform, e.g., in FIG. 9B, is initially assessed possibly after some filtering (e.g., bandpass filtering with cutoff frequencies of 0.5 to 10 Hz for the blood volume waveform). If the pressure applied 116 to the sensing unit 108 does not cover a wide enough range (e.g., at least 50 mmHg) over a sufficiently long time interval (e.g., at least 10 seconds) or the shape of the blood volume pulses often do not show physiologic character (i.e., a rapid rise followed by a slower decay), then the finger actuation may be deemed unsuccessful. In the event that multiple pressure sensors 532 are employed, the finger actuation could also be deemed unsuccessful, if the pressure experienced by each sensor is significantly different, as previously described. Otherwise, the multiple pressures may be averaged to yield a single pressure applied 116 to the sensing unit 108.

If the pressure applied 116 to the sensing unit 108 and blood volume waveform are considered to be of sufficient quality, the oscillogram 128 is constructed, for example by the oscillogram generator 308 of FIG. 3, according to any method known in the art of cuff BP measurement. For example, the pressure applied 116 to the sensing unit 108 is lowpass filtered or a polynomial is fitted to mitigate spurious fluctuations in the pressure applied 116 to the sensing unit 108. The maximum and minimum of each beat of the blood volume waveform are detected. These extrema, as a function of the pressure applied 116 to the sensing unit 108, are median filtered to attenuate respiratory and pulse rate variability as well as artifact. Finally, the extrema are linearly interpolated, and the difference between the two envelopes is taken as the oscillogram 128. If the oscillogram 128 does not exhibit physiologic character (e.g., uni-modal and smooth), the finger actuation may also be considered unsuccessful. For a physiologic oscillogram, a parametric model (e.g., single or multiple Gaussian functions or a quadratic function) may be fitted to yield a more robust oscillogram.

Finger BP is next estimated from successful oscillograms according to known algorithms in the art of oscillometry. For example, the basic maximum oscillation algorithm, the standard fixed-ratio algorithm seen in FIGS. 6A and 6B, the fixed-slope algorithm, or some combination or variant of the two may be employed. Alternatively, a patient-specific algorithm seen in FIGS. 7A and 7B, which may be more accurate than conventional population-based algorithms, may be applied. A third option is a combination of simple and more sophisticated algorithms. For example, a combined algorithm could output a MP estimate via the pressure applied 116 at which the oscillogram 128 is maximal when relatively low quality oscillograms are obtained and all three BP estimates via the patient-specific algorithm when higher quality oscillograms are measured. The algorithm could also output a confidence level on the accuracy of its BP estimates based on the measurement quality.

Standard brachial (arm) BP, which is the proven cardiovascular risk factor, may also be derived. While finger and brachial MP and DP are similar, finger SP is higher than brachial SP due to arterial wave reflection. Brachial SP may be estimated by simple transformations of finger BP. For example, since the ratio of finger SP to brachial SP may decrease with age, an age-dependent scaling of finger SP could be applied to estimate brachial SP. Alternatively, a transfer function may be applied to more accurately estimate brachial BP from finger BP. The transfer function would require input of the finger BP waveform, which could be obtained with the patient-specific algorithm. Another possibility is to estimate brachial SP from finger DP and MP using empirical formulas designed for brachial BP (e.g., MP=(1/3)*SP+(2/3)*DP).

Other physiologic parameters of interest such as pulse rate and pulse rate variability may also be computed from the blood volume waveform using any method known in the art. The pulse rate variability could be assessed to determine the presence of an arrhythmia such as atrial fibrillation using any method known in the art. If red and infrared PPG measurements are available, SpO2 may additionally be computed using an existing method.

Finally, an algorithm could also be employed for early termination of the finger actuation. For example, the oscillogram 128 could be constructed in real-time as the finger pressure is being applied. If the portion of the oscillogram that has been currently constructed is similar to the same portion of a previously constructed, complete oscillogram, then the previous BP levels could reasonably be assumed and immediately outputted. In this way, some BP measurements may only take a few seconds to make.

FIG. 14B is a diagram depicting a rectangular sensing unit 556. The rectangular sensing unit 556 includes a rectangular PPG sensor array 560 with multiple photodetectors 508 and one LED 512 and a rectangular pressure sensor array 566. The rectangular sensing unit 556 is placed on a side 570 of the encasing 520, which may be better suited to the finger pressing task.

Figure 15:
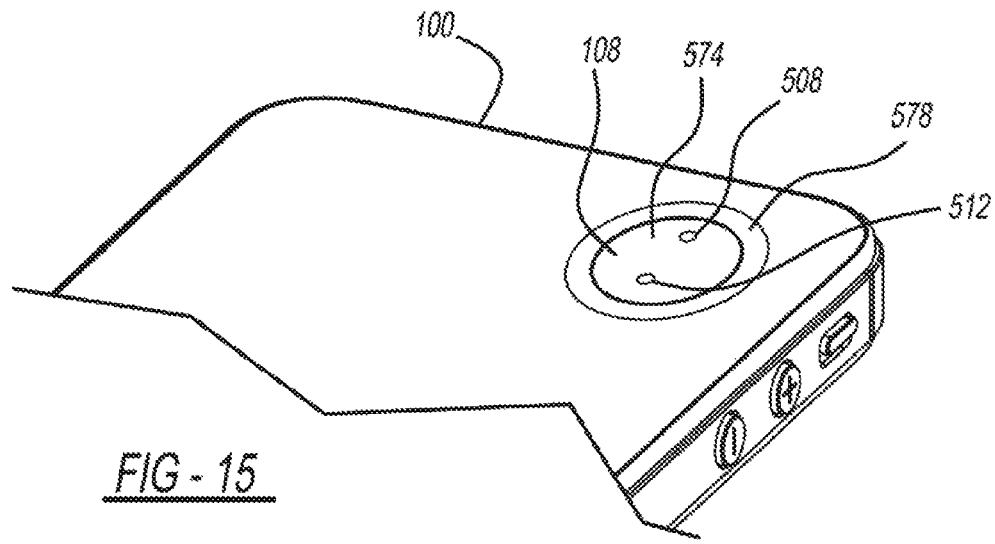
FIG. 15 is a diagram depicting another embodiment of the cuff-less BP measurement system on the mobile device.

FIG. 15 is a diagram depicting another embodiment of the cuff-less BP measurement system on the mobile device 100. For example, the mobile device 100 depicted in FIG. 15 is the same as the mobile device 100 of FIG. 1. However, instead of using the encasing 520 to couple the sensing unit 108 to the mobile device 100, the existing PPG sensor or the existing RGB camera 574 on the mobile device 100 is used. To complete the sensing unit, a donut shaped pressure sensor 578 is placed on top of and around the PPG sensor 574 to allow the passage of light.

Figure 16:
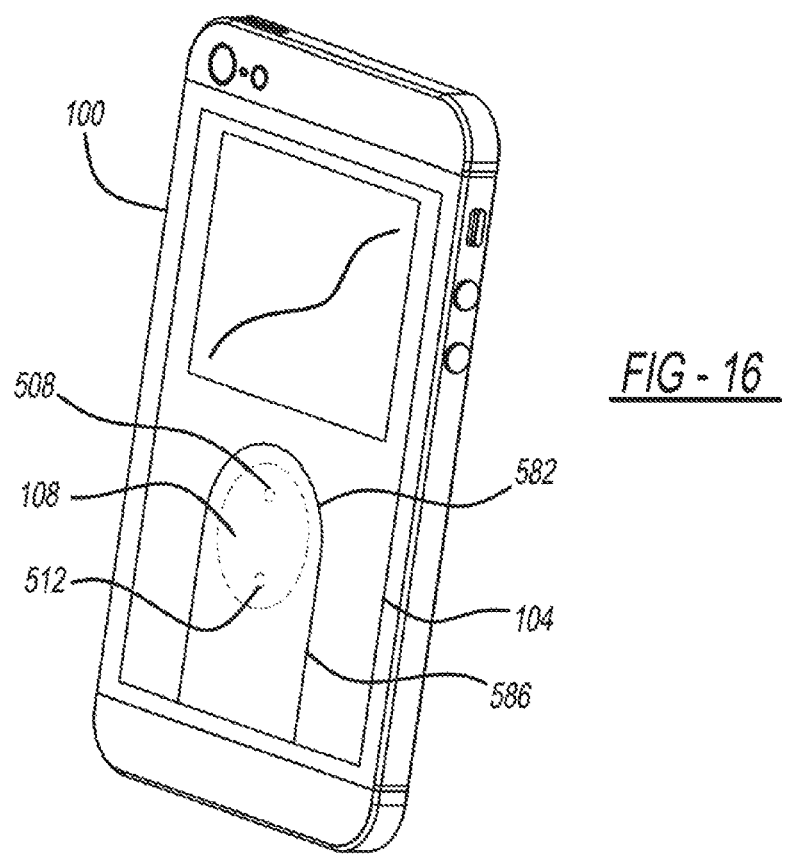
FIG. 16 is a diagram depicting another embodiment of the cuff-less BP measurement system.

FIG. 16 is a diagram depicting another embodiment of the cuff-less BP measurement system. FIG. 16 depicts the cuff-less BP measurement system with an infrared PPG sensor 582 located below the display 104 of the mobile device 100. The sensing unit 108, employing the infrared PPG sensor 582, could be placed under the display 104 while leveraging the pressure sensing capabilities of the display 104. In this case, a picture of the user's finger 586 could be displayed indicating exactly where the user should position their finger for subsequent pressing.

FIGS. 17A-17C are diagrams depicting an embodiment of the cuff-less BP measurement system with finger placement indicators. In FIG. 17A, the finger placement indicator 590 facilitates the finger positioning on the sensing unit 108 of the mobile device 100. The finger placement indicator 590 is a physical barrier placed around the sensing unit 108 to guide repeatable finger placement. The finger placement indicator 590 may be included on the encasing 520 or as a separate item attached to the mobile device 100 when using the RGB camera or PPG sensor of the mobile device 100. The finger placement indicator 590 could be adjustable to accommodate different finger sizes or multiple finger placement indicators 590 could be offered for different finger sizes (i.e., small, medium, and large). The finger placement indicator could also be a more subtle physical barrier than that indicated 590.

In FIG. 17B, a visual guide finger placement indicator 594 is placed on the mobile device 100. Alternatively, the visual guide finger placement indicator 594 may be on the encasing 520 of the mobile device 100. For example, lines could be drawn over the sensing unit 108 to guide the user in placing the base of the finger nail between the LED 512 and photodetector 508 and the center of the finger on the line passing through the LED 512 and photodetector 508, as also shown in FIG. 17C at 594. In addition, the sensing unit 108 may be positioned so that a portion of the finger below the top knuckle can also rest on the device to ensure normal direction force application.

The cuff-less BP measurement system, in any of the embodiments, may also be accompanied by additional means to guide proper finger actuation. In particular, proper finger placement for a specific user may be determined via an initialization protocol. This protocol involves measuring the oscillogram 128 at different finger positions on the sensing unit 108 and choosing the finger position based on the oscillogram amplitude and morphology (e.g., maximal oscillogram) or based on an initial cuff BP reading.

FIGS. 18A-18D are diagrams depicting an example position detection system included in the cuff-less BP measurement system. The camera that is already built in the mobile device 100 may be leveraged to ensure that the mobile device 100 is being held at heart level 600. The camera of the mobile device 100, as discussed above with respect to the RGB camera, may be used as a PPG sensor as well. For position detection purposes, the camera records an image of the face 604 while the mobile device 100 is known to be at heart level 600. For subsequent BP measurements, the camera records another image and compares the current image to the previously recorded image 604 known to be at heart level 600. The silhouette from the current image should be close enough to that of the previously recorded image. Otherwise, the application asks the user to put the mobile device at heart level. An example image when the mobile device 100 is below heart level 600 is shown at 608. This approach would only be effective when the user is in the upright posture. The accelerometer that is already in the mobile device 100 could also possibly be leveraged for confirming heart level 600.

In another embodiment, the cuff-less BP system may compensate for BP calculations when it has been detected that the user had their BP measured without holding the mobile device 100 at heart level. For example, after instructing the user to hold the mobile device 100 at heart level and then proceed to steadily increase the applied finger pressure, the system measures and records BP measurements. If the system detects that the mobile device 100 is not being held at heart level, then the recorded BP measurements can be adjusted accordingly for the height at which the measurements were being taken using a rho-g-h correction, where rho is the known blood density, g is gravity, and h is the vertical distance between the finger and heart estimated from the images.

Figure 19:
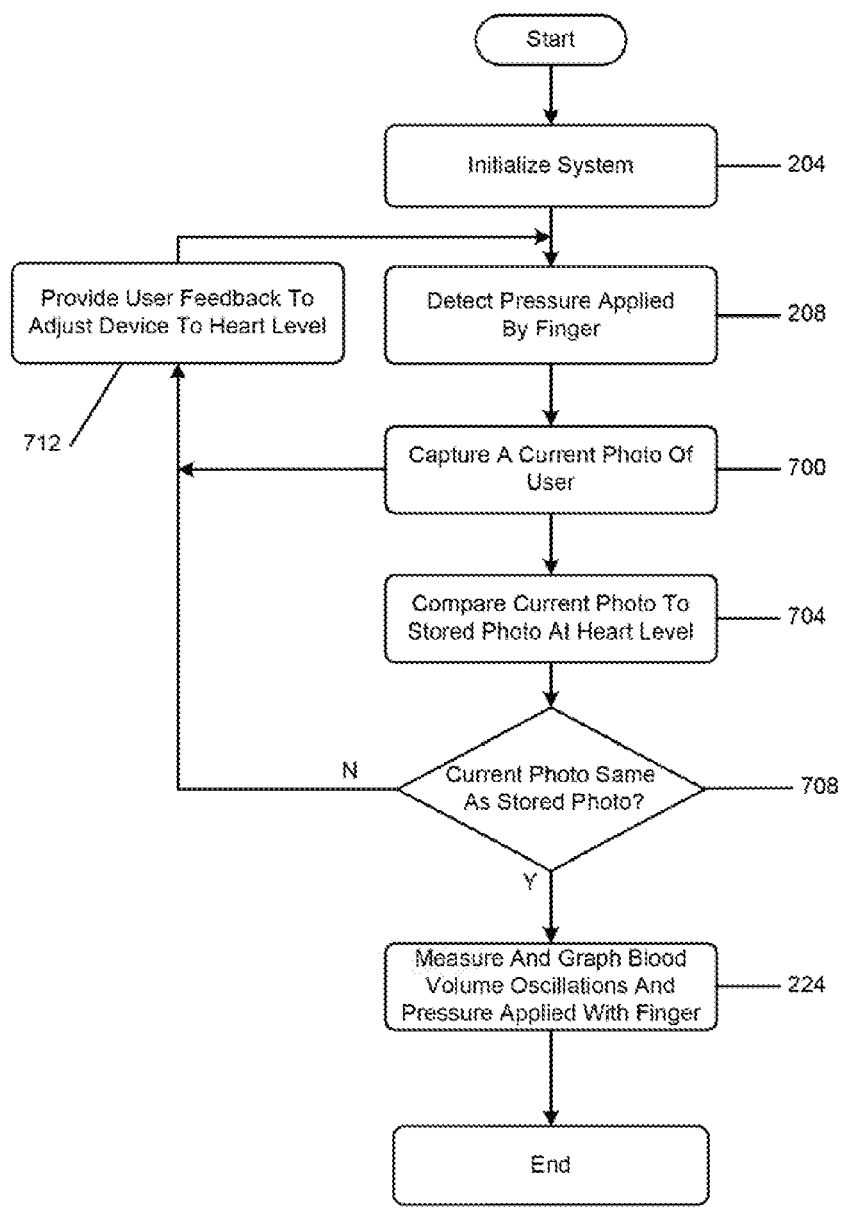
FIG. 19 is a flowchart depicting the example position detection system included in the cuff-less BP measurement system.

FIG. 19 is a flowchart depicting the example position detection system included in the cuff-less BP measurement system. The system is initialized at 204 and the pressure applied 116 by the finger is detected at 208. To ensure that the user is holding the mobile device 100 at heart level, the system captures a current photo 608 of the user at 700. The system then compares the current photo 608 to a previously recorded or stored photo 604 of the user when the mobile device 100 is known to be held at heart level at 704. If the current photo 608 is the same as or similar enough to the previously recorded photo 604, then the system continues to measure and graph blood volume oscillations and pressure applied 116 to the sensing unit 108 with the finger at 224. If, however, the current photo 608 differs from the previously recorded photo 604 by a predetermined amount, then the system provides feedback to the user instructing to user to adjust the mobile device 100 to heart level at 712. In an embodiment, the photos that are captured may be silhouettes or outlines to be able to compare a size of the user to determine if the mobile device 100 is at heart level.

As another example to guide proper finger actuation, a fingerprint could be taken and used to confirm and/or guide proper finger positioning on the sensing unit 108 as well as to identify the user for a multi-user device. Maintaining an identity of users ensures measurements are transmitted to the appropriate place. In addition, the application could include an instructional video to explain how to use the device correctly. Alternatively, the user could test for the best finger position by measuring the user's BP multiple times and recording the finger position each time. After at least two attempts to measure the user's BP, the application could determine which BP measurement results in the largest oscillogram and indicate to the user that the recorded finger position for the largest oscillogram is the preferred finger position for that user.

In other embodiments, the mobile device 100 could act as the actuator instead of the user. For example, the mobile device 100 could include a motor driven system or a mechanical spring that would automatically apply the pressure to the finger placed on the sensing unit 108. Additionally, the method could also be integrated within non-mobile device form factors including elevator control panels, video game controllers, doorbells, keychains, steering wheels, bathroom mirrors, pill bottle caps, etc.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a computer selectively activated or reconfigured by a computer program stored on a computer readable medium that can be accessed by the computer. Such a computer program may be stored in a tangible computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatuses to perform the required method steps. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system for measuring blood pressure, comprising:
a mobile device including a processor and a display unit; and
an encasing configured to encase the mobile device, wherein the encasing includes:
a sensing unit integrated into the encasing and configured to measure blood pressure at a fingertip of a user, wherein the sensing unit includes a reflectance-mode photo-plethysmography (PPG) sensor configured to measure blood volume oscillations and a force sensor configured to measure pressure applied by the fingertip; and
a visual guide disposed on the encasing and arranged in relation to the sensing unit, where the visual guide comprise indicia to guide the user in placing a base of fingernail and a center of the finger in relation to the sensing unit;
wherein the system includes a non-transitory computer-readable medium that stores instructions that, when executed by the processor, cause the processor to:
measure pressure applied to the sensing unit by a fingertip of a user,
measure blood volume oscillations in the fingertip,
guide the user via the display unit to vary pressure being applied to the sensing unit while the blood volume oscillations and pressure are measured,
generate an oscillogram from the measured pressure and the measured blood volume oscillations, where the oscillogram plots amplitude of blood volume oscillations as a function of the measured pressure,
calculate a blood pressure value from the oscillogram, and
present the blood pressure value on the display unit.

2. The system of claim 1 wherein the PPG sensor includes at least one light emitting diode and an array of photodetectors.

3. The system of claim 2 wherein the maximum amplitude photodetector signal is used as the blood volume oscillations.

4. The system of claim 1 wherein the force sensor is an array of force transducer elements.

5. The system of claim 4 wherein an area of force application is determined based on the force outputs of each element.

6. The system of claim 1 wherein the sensing unit further includes a temperature sensor.

7. The system of claim 1 further includes instructions that, when executed by the processor, cause the processor to guide the user to hold the device at a height aligned with the heart of the user.

8. The system of claim 7 further includes instructions that, when executed by the processor, cause the processor to capture an image of the user with a camera, compare the captured image to a reference image of the user, and instruct the user to hold the mobile device at a height aligned with the heart of the user based on the comparison of the captured image with the reference image, where the reference image was captured when the device was being held at a height aligned with the heart of the user.

9. The system of claim 1 further includes instructions that, when executed by the processor, cause the processor to capture an image of the user with a camera, compare the captured image to a reference image of the user, detect the height at which the device is being held relative to the heart based on the comparison of the captured image with the reference image, where the reference image was captured when the device was being held at a height aligned with the heart of the user, and compensate the calculated blood pressure value in accordance with the detected height.

10. The system of claim 1 wherein the processor generates a blood pressure value by
representing the oscillogram with a mathematical model, wherein the mathematical model is defined in terms of parameters with unknown values, the parameters indicating finger systolic pressure and finger diastolic pressure and specifying a nonlinear blood volume-transmural pressure relationship of a fingertip artery;
estimating the parameters of the mathematical model by fitting the mathematical model to the oscillogram; and
computing brachial systolic pressure and diastolic pressure using the parameter estimates.

11. The system of claim 10 wherein computing brachial systolic pressure and diastolic pressure further comprises use of a transfer function.

12. A system for measuring blood pressure, comprising:
a mobile device including a processor and a display unit; and
an encasing configured to encase the mobile device, wherein the encasing includes:
a sensing unit integrated into the encasing and configured to measure blood pressure at a fingertip of a user, wherein the sensing unit includes a reflectance-mode photo-plethysmography (PPG) sensor configured to measure blood volume oscillations and a force sensor configured to measure pressure applied by the fingertip; and
a visual guide disposed on the encasing and arranged in relation to the sensing unit, where the visual guide comprise indicia to guide the user in placing a surface of the fingertip on an opposite side of the finger from a fingernail on the finger and distal from a distal interphalangeal joint of the finger onto the sensing unit;
wherein the system includes a non-transitory computer-readable medium that stores instructions that, when executed by the processor, cause the processor to:
measure pressure applied to the sensing unit by a fingertip of a the user,
measure blood volume oscillations in the fingertip,
guide the user via the display unit to vary pressure being applied to the sensing unit while the blood volume oscillations and pressure are measured,
generate an oscillogram from the measured pressure and the measured blood volume oscillations, where the oscillogram plots amplitude of blood volume oscillations as a function of the measured pressure,
calculate a blood pressure value at level of brachial artery from the oscillogram, and
present the blood pressure value on the display unit.

13. The system of claim 10 further comprises using a transfer function to calculate the blood pressure value at the level of brachial artery.

* * * * *